(12) United States Patent
Green et al.

(10) Patent No.: US 10,604,587 B2
(45) Date of Patent: Mar. 31, 2020

(54) GENETIC ENGINEERING OF NON-HUMAN ANIMALS FOR THE PRODUCTION OF CHIMERIC ANTIBODIES

(71) Applicant: ABLEXIS, LLC, San Diego, CA (US)

(72) Inventors: Larry Green, San Francisco, CA (US); Hiroaki Shizuya, South Pasadena, CA (US)

(73) Assignee: ABLEXIS, LLC, San Diego, CA (US)

( * ) Notice: Subject to any disclaimer, the term of this patent is extended or adjusted under 35 U.S.C. 154(b) by 0 days.

(21) Appl. No.: 15/463,800

(22) Filed: Mar. 20, 2017

(65) Prior Publication Data

US 2017/0190796 A1    Jul. 6, 2017

Related U.S. Application Data

(62) Division of application No. 15/408,114, filed on Jan. 17, 2017, now Pat. No. 10,494,445, which is a division of application No. 13/638,522, filed as application No. PCT/US2011/030823 on Mar. 31, 2011, now Pat. No. 9,580,491.

(60) Provisional application No. 61/361,302, filed on Jul. 2, 2010, provisional application No. 61/319,690, filed on Mar. 31, 2010.

(51) Int. Cl.
*A01K 67/027* (2006.01)
*C07K 16/46* (2006.01)
*C07K 16/00* (2006.01)
*C07K 16/18* (2006.01)
*C12N 15/85* (2006.01)

(52) U.S. Cl.
CPC ........ *C07K 16/461* (2013.01); *A01K 67/0275* (2013.01); *A01K 67/0278* (2013.01); *C07K 16/00* (2013.01); *C07K 16/18* (2013.01); *C12N 15/8509* (2013.01); *A01K 2207/15* (2013.01); *A01K 2217/052* (2013.01); *A01K 2217/072* (2013.01); *A01K 2227/105* (2013.01); *A01K 2267/01* (2013.01); *C07K 2317/14* (2013.01); *C07K 2317/24* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2317/64* (2013.01); *C12N 2510/02* (2013.01)

(58) Field of Classification Search
CPC .............................................. A01K 67/0278
See application file for complete search history.

(56) References Cited

U.S. PATENT DOCUMENTS

| | | |
|---|---|---|
| 5,204,244 A | 4/1993 | Fell |
| 5,464,764 A | 11/1995 | Capecchi et al. |
| 5,487,992 A | 1/1996 | Capecchi et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,669 A | 1/1997 | Krimpenfort |
| 5,612,205 A | 3/1997 | Kay et al. |
| 5,625,126 A | 4/1997 | Lonberg et al. |
| 5,627,059 A | 5/1997 | Capecchi et al. |
| 5,631,153 A | 5/1997 | Capecchi et al. |
| 5,633,425 A | 5/1997 | Lonberg et al. |
| 5,654,182 A | 8/1997 | Wahl et al. |
| 5,661,016 A | 8/1997 | Lonberg et al. |
| 5,677,177 A | 10/1997 | Wahl et al. |
| 5,721,367 A | 2/1998 | Kay et al. |
| 5,770,429 A | 6/1998 | Lonberg et al. |
| 5,789,215 A | 8/1998 | Berns et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,836 A | 3/1999 | Wahl et al. |
| 5,939,598 A | 8/1999 | Kucherlapati et al. |
| 6,023,010 A | 2/2000 | Krimpenfort et al. |
| 6,075,181 A | 6/2000 | Kucherlapati et al. |
| 6,090,554 A | 7/2000 | Woychik et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,150,584 A | 11/2000 | Kucherlapati et al. |
| 6,162,963 A | 12/2000 | Kucherlapati et al. |

(Continued)

FOREIGN PATENT DOCUMENTS

| | | |
|---|---|---|
| EP | 1399559 | 4/2008 |
| WO | WO 90/00616 | 4/1990 |

(Continued)

OTHER PUBLICATIONS

Sun et al., 2012, J. Animal Sci. and Biotech., vol. 3(18), pp. 1-5 (Year: 2012).*

(Continued)

*Primary Examiner* — Thaian N. Ton
*Assistant Examiner* — David A. Montanari
(74) *Attorney, Agent, or Firm* — Haley Guiliano LLP; James F. Haley, Jr.; Brian M. Gummow

(57) ABSTRACT

The invention provides non-human cells and mammals having a genome encoding chimeric antibodies and methods of producing transgenic cells and mammals. Certain aspects of the invention include chimeric antibodies, humanized antibodies, pharmaceutical compositions and kits. Certain aspects of the invention also relate to diagnostic and treatment methods using the antibodies of the invention.

19 Claims, 5 Drawing Sheets

(56) References Cited

U.S. PATENT DOCUMENTS

| | | |
|---|---|---|
| 6,204,061 B1 | 3/2001 | Capecchi et al. |
| 6,348,349 B1 | 2/2002 | Bruggemann |
| 6,528,313 B1 | 3/2003 | Le Mouellic et al. |
| 6,528,314 B1 | 3/2003 | Le Mouellic et al. |
| 6,570,061 B1 | 5/2003 | Rajewsky et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,638,768 B1 | 10/2003 | Le Mouellic et al. |
| 6,653,113 B1 | 11/2003 | Berns et al. |
| 6,657,103 B1 | 12/2003 | Kucherlapati et al. |
| 6,673,986 B1 | 1/2004 | Kucherlapati et al. |
| 6,689,610 B1 | 2/2004 | Capecchi et al. |
| 6,774,279 B2 | 8/2004 | Dymecki |
| 6,794,132 B2 | 9/2004 | Buechler et al. |
| 6,833,268 B1 | 12/2004 | Green et al. |
| 6,852,530 B2 | 2/2005 | Silver et al. |
| 6,956,146 B2 | 10/2005 | Wahl et al. |
| 6,998,514 B2 | 2/2006 | Bruggemann |
| 7,041,870 B2 | 5/2006 | Tomizuka et al. |
| 7,041,871 B1 | 5/2006 | Lonberg et al. |
| 7,049,426 B2 | 5/2006 | Green et al. |
| 7,064,244 B2 | 6/2006 | Jakobovits et al. |
| 7,105,348 B2 | 9/2006 | Murphy et al. |
| 7,145,056 B2 | 12/2006 | Jakobovits et al. |
| 7,205,148 B2 | 4/2007 | Economides et al. |
| 7,235,360 B2 | 6/2007 | Reff et al. |
| 7,371,577 B2 | 5/2008 | Wahl et al. |
| 7,435,871 B2 | 10/2008 | Green et al. |
| 7,501,552 B2 | 6/2009 | Bruggeman et al. |
| 7,541,513 B2 | 6/2009 | Bruggeman et al. |
| 7,547,817 B2 | 6/2009 | Green et al. |
| 7,722,871 B2 | 5/2010 | Casterman |
| 7,910,798 B2 | 3/2011 | Tanamachi et al. |
| 8,629,317 B2 | 1/2014 | Cogne |
| 8,754,287 B2 | 6/2014 | Macdonald |
| 9,346,873 B2 | 5/2016 | Green et al. |
| 9,365,655 B2 | 6/2016 | Craig et al. |
| 9,445,581 B2 | 9/2016 | Bradley |
| 9,580,491 B2 | 2/2017 | Green et al. |
| 2003/0135872 A1 | 7/2003 | Burgess, Jr. et al. |
| 2003/0222218 A1 | 12/2003 | Nozu |
| 2003/0229905 A1 | 12/2003 | Kucherlapati et al. |
| 2004/0025031 A1 | 2/2004 | Ooi et al. |
| 2004/0107452 A1 | 6/2004 | Berns et al. |
| 2004/0128703 A1 | 7/2004 | Shizuya |
| 2004/0203153 A1 | 10/2004 | Le Mouellic et al. |
| 2004/0214222 A1 | 10/2004 | Burgess, Jr. et al. |
| 2004/0231012 A1 | 11/2004 | Bruggemann |
| 2005/0038232 A1 | 2/2005 | Karrer et al. |
| 2005/0118648 A1 | 6/2005 | Li |
| 2005/0149998 A1 | 7/2005 | Capecchi et al. |
| 2005/0238645 A1 | 10/2005 | Gold et al. |
| 2005/0261480 A1 | 11/2005 | Foote |
| 2006/0015949 A1 | 1/2006 | Lonberg et al. |
| 2006/0015957 A1* | 1/2006 | Lonberg ............ A01K 67/0275 800/18 |
| 2006/0040363 A1 | 2/2006 | Kucherlapati et al. |
| 2006/0117398 A1 | 6/2006 | Buelow et al. |
| 2006/0134780 A1 | 6/2006 | Green et al. |
| 2007/0009957 A1 | 1/2007 | Bowdish |
| 2007/0061900 A1 | 3/2007 | Murphy et al. |
| 2007/0092505 A1 | 4/2007 | Buelow et al. |
| 2007/0209083 A1 | 9/2007 | Thiam |
| 2008/0098490 A1 | 4/2008 | Jakobovits et al. |
| 2008/0182331 A1 | 7/2008 | Le Mouellic et al. |
| 2009/0098134 A1* | 4/2009 | Buelow ............ A01K 67/0278 424/141.1 |
| 2009/0260093 A1 | 10/2009 | Tanamachi |
| 2010/0077497 A1 | 3/2010 | deshpande |
| 2010/0287629 A1 | 11/2010 | Lonberg et al. |
| 2011/0236378 A1 | 9/2011 | Green et al. |
| 2012/0070861 A1 | 3/2012 | Macdonald et al. |
| 2013/0167256 A1 | 6/2013 | Green et al. |
| 2016/0219848 A1 | 8/2016 | Green et al. |
| 2016/0219849 A1 | 8/2016 | Green et al. |
| 2016/0219850 A1 | 8/2016 | Green et al. |
| 2016/0222090 A1 | 8/2016 | Green et al. |
| 2016/0222091 A1 | 8/2016 | Green et al. |
| 2016/0222092 A1 | 8/2016 | Green et al. |
| 2016/0222093 A1 | 8/2016 | Green et al. |
| 2017/0181414 A1 | 6/2017 | Green et al. |
| 2017/0188557 A1 | 7/2017 | Green et al. |
| 2017/0188558 A1 | 7/2017 | Green et al. |
| 2017/0190794 A1 | 7/2017 | Green et al. |
| 2017/0190795 A1 | 7/2017 | Green et al. |
| 2017/0190797 A1 | 7/2017 | Green et al. |
| 2017/0218090 A1 | 8/2017 | Green et al. |

FOREIGN PATENT DOCUMENTS

| | | | |
|---|---|---|---|
| WO | WO 1990/004036 | 4/1990 | |
| WO | WO 90/04036 | 10/1990 | |
| WO | WO 90/11354 | 1/1991 | |
| WO | WO 91/00906 | 1/1991 | |
| WO | WO 91/10741 | 7/1991 | |
| WO | WO 91/19796 | 12/1991 | |
| WO | WO 92/03917 | 3/1992 | |
| WO | WO 92/03918 | 3/1992 | |
| WO | WO 93/12227 | 6/1993 | |
| WO | WO 94/02602 | 2/1994 | |
| WO | WO 94/25585 | 11/1994 | |
| WO | WO 96/30498 | 10/1996 | |
| WO | WO 96/33735 | 10/1996 | |
| WO | WO 96/34096 | 10/1996 | |
| WO | WO 97/13852 | 4/1997 | |
| WO | WO 98/24884 | 6/1998 | |
| WO | WO 98/24893 | 6/1998 | |
| WO | WO 99/45962 | 9/1999 | |
| WO | WO 00/26373 | 5/2000 | |
| WO | WO 00/76310 | 12/2000 | |
| WO | WO 02/12437 | 2/2002 | |
| WO | WO 02/43478 | 6/2002 | |
| WO | WO 02/66630 | 8/2002 | |
| WO | WO 2003/002725 | 1/2003 | |
| WO | WO 2003/027261 | 4/2003 | |
| WO | WO 2003/047336 | 6/2003 | |
| WO | WO 2003/048346 | 6/2003 | |
| WO | WO 2004/076618 | 9/2004 | |
| WO | WO 2004/078937 | 9/2004 | |
| WO | WO 2005/019463 | 3/2005 | |
| WO | WO 2006/072803 | 7/2006 | |
| WO | WO 2006/117699 | 11/2006 | |
| WO | WO 2007/024715 | 3/2007 | |
| WO | WO-2007024715 A2 * | 3/2007 | ........... C07K 16/241 |
| WO | WO 2007/117410 | 10/2007 | |
| WO | WO2007117410 | 10/2007 | |
| WO | WO 2008/027986 | 3/2008 | |
| WO | WO 2008/090958 | 7/2008 | |
| WO | WO 2008/151081 | 12/2008 | |
| WO | WO 2009/143472 | 11/2009 | |
| WO | WO 2009/157771 | 12/2009 | |
| WO | WO 2010/03990 | 4/2010 | |
| WO | WO 2010/039900 | 4/2010 | |
| WO | WO 2010/070263 | 6/2010 | |
| WO | WO 2011/004192 | 1/2011 | |
| WO | WO 2011/123708 | 10/2011 | |
| WO | WO 2011/158009 A1 | 12/2011 | |

OTHER PUBLICATIONS

Ivics et al. (2014, Nature Protocols, vol. 9(4), pp. 810-827) (Year: 2014).*

Meng et al. (2015, J. Animal Sci. and Biotech., pp. 1-7) (Year: 2015).*

Brevini et al., 2010, Theriogenology, vol. 74, pp. 544-550 (Year: 2010).*

Paris et al. (2010, Theriogenology, vol. 74, pp. 516-524) (Year: 2010).*

Munoz et al. (2008, Theriogenology, vol. 69, pp. 1159-1164) (Year: 2008).*

Gomez et al. (2010, Theriogenology, vol. 74, pp. 498-515) (Year: 2010).*

(56) References Cited

OTHER PUBLICATIONS

Buta et al. (2013, Stem Cell Res., vol. 11, pp. 552-562) (Year: 2013).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*
Bankovich, A.J., et al., "Structural Insight into Pre-B Cell Receptor Function." Science (2007); 316(Issue 5822): 291-294.
Buchner, D.A., et al., "High-resolution mapping of the sodium channel modifier Scnm1 on mouse chromosome 3 and identification of a 1.3-kb recombination hot spot." Genomics (2003); 82(4): 452-459.
Chauveau, C., et al., "Synergies between regulatory elements of the immunoglobulin heavy chain locus and its palindromic 3' locus control region." Eur J Immunol. (1998); 28(10): 3048-3056.
Crawley, J.N., "What's Wrong With My Mouse? Behavioral Phenotyping of Transgenic and Knockout Mice." Wiley-Interscience, John Wiley & Sons (2007), pp. 21-29, 12 pages.
Definition of SYNGENEIC by Merriam-Webster downloaded Aug. 8, 2017; pp. 1-9.
Felgenhauer, M., et al., "Nucleotide sequences of the cDNAs encoding the V-regions of H- and L-chains of a human monoclonal antibody specific to HIV-1-gp41." Nucleic Acids Res. (1990); 18(16): 4927.
Gama Sosa, M.A., et al., "Animal transgenesis: an overview." Brain Struct Funct (2010); 214: 91-109.
Geier and Schlissel. "Pre-BCR signals and the control of Ig gene rearrangements." Seminars in immunology (2006); 18: 31-39.
Grange and Boyes, "Chromatin opening is tightly linked to enhancer activation at the kappa light chain locus." Biochem Biophys Res Commun. (2007); 363(1): 223-228.
Hirabayashi, Y., et al., "Kinetic analysis of the interactions of recombinant human VpreB and Ig V domains." J Immunol (1995); 155:1218-1228.
Hybridoma Technology—Wikipedia Hybridoma technology From Wikipedia, the free encyclopedia pp. 1-4; downloaded Jun. 26, 2017.
Jefferis, R., "Recombinant antibody therapeutics: the impact of glycosylation on mechanisms of action." Trends in Pharmacological Sciences (2009); 30(7): 356-362.
Johnson, K., et al., "Regulatory events in early and late B-cell differentiation." Mol Immunol. (2005); 42(7):749-761.
Labrijin, A.F., et al., "Therapeutic IgG4 antibodies engage in Fab-arm exchange with endogenous human IgG4 in vivo." Nat Biotechnol. (2009); 27(8): 767-771, 7 pages.
Lefranc, M.P., "Nomenclature of the human immunoglobulin genes." Curr Protoc Immunol. (2000); Supplement 40, pp. 1-37.
Lightle, S., et al., "Mutations within a human IgG2 antibody form distinct and homogeneous disulfide isomers but do not affect Fc gamma receptor or C1q binding." Protein Science (2010); 19(4): 753-762.
Manis, J.P., et al., "Class Switching in B Cells Lacking 3' Immunoglobulin Heavy Chain Enhancers." The Journal of Experimental Medicine (1998); 188(8): 1421, pp. 1-27.
Moran, N., "Mouse platforms jostle for slice of humanized antibody market." Nature Biotechnology (2013); 31(4): 267-268.
Murphy and Silha, "Unexpected and unexplained phenotypes in transgenic models." Growth Hormone & IGF Research (2000); 10:: 233-235.
Reddy, M.P., et al., "Elimination of Fc receptor-dependent effector functions of a modified IgG4 monoclonal antibody to human CD4." J Immunol. (2000); 164(4): 1925-1933.
Ristevski, S., "Making better transgenic models: conditional, temporal, and spatial approaches." Molecular Biotechnology (2005); 29(2): 153-163.
Roitt, I., et al., Essential Immunology, Ch. 3, Sxith Edition, Blackwell Scientific Publications (1988); pp. 31-35.
Roopenian and Akilesh, "FcRn: the neonatal Fc receptor comes of age." Nature Reviews. Immunology (2007); 7: 715-25.
Salfeld, J.G., "Isotype selection in antibody engineering." Nature Biotechnology (2007); 25: 1369-1372.
Sandin, et al., "Structure and Flexibility of Individual Immunoglobulin G Molecules in Solution," Structure (2004); 12: 409-415.
Schuurman, J., et al., "The inter-heavy chain disulfide bonds of IgG4 are in equilibrium with intra-chain disulfide bonds." Mol Immunol. (2001); 38(1): 1-8.
Scott, C.T., "Mice with a human touch." Nature (2007); 25(10):1075-1077.
Sigmund, C.D., "Viewpoint: are studies in genetically altered mice out of control?" Arterioscler. Thromb. Vasc. Biol. (2000); 20(6): 1425-1429.
Smith, K.R., "Gene transfer in higher animals: theoretical considerations and key." Journal of Biotechnology (2002); 99: 1-22.
Vettermann and Schlissel, "Allelic exclusion of immunoglobulin genes: models and mechanisms." Immunol Rev. (2010); 237(1): 22-42.
Xu, Y., et al. "Deletion of the Igκ light chain intronic enhancer/matrix attachment region impairs but does not abolish VκJκ rearrangement." Immunity (1996); 4(4): 377-385.
Yang and Ross, Genetic Modification of Domestic Animals for Agriculture and Biomedical applications, Biomedical Science, Engineering and Technology; Prof Dhanjoo Ghista (Ed) in Tech Publisher (2012); pp. 699-726.
Cameron, "Recent Advances in Transgenic Technology," Molecular Biotechnology, 7:253-265 (1977).
Giraldo, et al., "Size matters: use of YACs, BACs and PACs in transgenic animals," Transgenic Research, 10(2):83-103 (2001).
Goldman, et al., "Transgenic animals in medicine: integration and expression of foreign genes, theoretical and applied aspects," Medical Science Monitor, 10(11):RA274-275 (2004).
Houdebine, "Production of pharmaceutical proteins from transgenic animals," Journal of Biotechnology, 34(3):269-87 (1994).
Houdebine, "The methods to generate transgenic animals and to control transgene expression," Journal of Biotechnology, 98(2-3):145-160 (2002).
Kappel, et al., "Regulating gene expression in transgenic animals," Current Opinions in Biotechnology, 3(5):548-553 (1992).
Kolb, et al., "Insertion of a foreign gene into the beta-casein locus by Cre-mediated site-specific recombination," Gene, 227(2):21-31 (1999).
Mullins, et al., "Transgenesis in Nonmurine Species," Hypertension, 22(4):630-633 (1993).
Das, S., et al., "Analysis of the Immunoglobulin Light Chain Genes in Zebra Finch: Evolutionary Implications." Molecular Biology and Evolution (2010); 27(1): 113-120.
Extended European Search Report for European Patent Application No. 17178066.1 dated Oct. 12, 2017, 9 pages.
Extended European Search Report for European Patent Application No. 17178088.5 dated Oct. 13, 2017, 9 pages.
Hafler et al., "Anti-CD4 and anti-CD2 monoclonal antibody infusions in subjects with multiple sclerosis. Immunosuppressive effects and human anti-mouse responses." J Immunol (1988); 141(1): 131-138; Abstract.
Ivics, Z., et al., "Germline transgenesis in pigs by cytoplasmic microinjection of Sleeping Beauty transposons." Nature Protocols (2014); 9: 810-827.
Meng, F., et al., "Optimized production of transgenic buffalo embryos and offspring by cytoplasmic zygote injection." J. Animal Sci. and Biotech. (2015); 6: 44, 7 pages.
Sun, Y., et al., "Immunoglobulin genes and diversity: what we have learned from domestic animals." J. Animal Sci. and Biotech. (2012); 3(18): 1-5.
West and Gill, "Genome editing in large animals." J. Equine Vet. Sci. (2016); 41: 1-6, 12 pages.
Yu, X., et al., "An optimized electrofusion-based protocol for generating virus-specific human monoclonal antibodies." J. Immunol. Methods (2008); 336(2): 142-151.
Brekke, et al., "Structure-Function Relationships of Human IgG," Immunologist, 2:125-130 (1994).
Brekke, et al., "The structural requirements for complement activation by IgG: does it hinge on the hinge?," Immunology Today, 16(2): 85-90 (1995).

(56) References Cited

OTHER PUBLICATIONS

Briere, et al, "Human interleukin 10 induces naive surface immunoglobulin D+ (sIgD+) B cells to secrete IgG1 and IgG3," Journal of Experimental Medicine, 179(2):757-762 (1994).
Burton, "Structure and function of antibodies," New Comprehensive Biochemistry, 17(1):1-50 (1987).
Das, et al., "Analysis of the immunoglobulin light chain genes in zebra finch: evolutionary implications," Molecular Biology and Evolution, 27(1):113-120 (2010).
Ivics, et al., "Germline transgenesis in pigs by cytoplasmic microinjection of Sleeping Beauty transposons," Nature Protocols, 9(4):810-827 (2014).
Kim, et al., "Catabolism of the murine IgG1 molecule: evidence that both CH2-CH3 domain interfaces are required for persistence of IgG1 in the circulation of mice," Scandinavian Journal of Immunology, 40(4):457-465 (1994).
Krawinkel, et al., Comparison of the hinge-coding segments in human immunoglobulin gamma heavy chain genes and the linkage of the gamma 2 and gamma 4 subclass genes, EMBO Journal, 1(4):403-407 (1982).
Meng, et al., "Optimized production of transgenic buffalo embryos and offspring by cytoplasmic zygote injection," Journal of Animal Science and Biotechnology, 6:44 (7 pages) (2015).
Pradhan, et al., "An Efficient Method for Generation of Transgenic Rats Avoiding Embryo Manipulation." Molecular Therapy-Nucleic Acids 5: e293 (11 pages) (2016).
Sun, et al., "Immunoglobulin genes and diversity: what we have learned from domestic animals," Journal of Animal Science and Biology, 3(18):1-5 (2012).
West, et al., "Genome editing in large animals," Journal of Equine Veterinary Science, 41:1-6 (2016).
Yu, et al., "An optimized electrofusion-based protocol for generating virus-specific human monoclonal antibodies," Journal of Immunological Methods, 336(2):142-151 (2008).
Afshar et al., "Regulation of IgH Gene Assembly: Role of the Intronic Enhancer and 5 $D_{Q52}$ Region in Targeting $D_H J_h$ Recombination[1]," J. Immunol. (2006) 176: 2439-2447.
Antibody—Wikipedia, the free encyclopedia, last visited Jan. 23, 2014, http://en.wikipedia.org/wiki/Antibody, 19 pages.
Askew et al., "Site-Directed Point Mutations in Embryonic Stem Cells: a Gene-Targeting Tag-and-Exchange Strategy," Molecular and Cellular Biology 13(7):4115-4124, 1993.
Behringer et al., "Human γ- to β-globin gene switching in transgenic mice," Genes & Development 4:380-389, 1990.
Berman, et al., "Content and organization of the human 19 VH IOCUS: definition of three new VH families and linkage to the Ig CH Locus," The EMBO Journal, 7(3):727-738 (1988).
Blaas et al., "Bacterial artificial chromosomes improve recombinant protein production in mammalian cells," BMC Biotechnology 9(3):1-5, 2009.
Bruggeman et al., "A repertoire of monoclonal antibodies with human heavy chains from transgenic mice" PNAS, (1989), 86:6709-6713.
Capecchi, "Generating mice with targeted mutations," Nature Medicine 7(10):1086-1090, 2001.
Capecchi, "The New Mouse Genetics: Altering the Genome by Gene Targeting," Trends in Genetics 5(3):70-76, 1989.
Carosella, E.D., et. al., "Anti-Human interleukin 2 receptor monoclonal antibody isotypic switching: chimeric rat-human antibodies," Human Immunology, 29:233-246, (1990).
Chan et al.,"Epitope mapping of a chimeric CD137 mAb: a necessary step for assessing the biologic relevance of non-human primate models," J Mol Recognit, (2009), 22(3):242-249.
Chen et al. "Immunoglobulin gene rearrangement in B cell deficient mice generated by targeted deletion of the $J_H$ locus," EMBO J., (1993) 12: 821-830.
Chen J., et al. "B cell development in mice that lack one or both immunoglobulin x light chain genes," Int Immunol., Jun. 1993;5(6):647-56.

Combriato and Klobeck,"Regulation of Human Igλ Light Chain Gene Expression by NF-κB[1]," J. Immunol. (2002), 168(3):1259-1266.
Extended European Search Report and Search Opinion for EP2346994, dated Feb. 9, 2012.
Extended European Search Report and Search Opinion for Eurpoean Patent Application 11763476.6, dated Sep. 20, 2013, 7 pages.
Fell et al., "Homologous recombination in hybridoma cells: Heavy chain chimeric antibody produced by gene targeting," Proc. Natl. Acad. Sci. USA 86:8507-8511, 1989.
Fishwild et al., "High-avidity humak IgGκ monoclonal antibodies from a novel strain of minilocus transgenic mice," Nat Biotechnol, (1996) 14:845-851.
Frippiat et al. "Organization of the human immunoglobulin lambda light-chain locus on chromosome 22q11.2," Hum. Mol. Genet. (1995) 4: 983-991.
Hunter, et al., "Generation of canine-human Fc IgE chimeric antibodies for the determination of the canine IgE domain of interaction with FcεRIα," Molecular Immunology, 45:2262-2268 (2008).
Hunter, M.J., et al., "Generation of canine-human Fc IgE chimeric antibodies for the determination of the canine IgE domain of interaction with Fc epsilon Rl alpha," Molecular Immunology, 45:2262-2268 (2008).
International Preliminary Report on Patentability for PCT/US2009/059131, dated Apr. 14, 2011.
International Preliminary Report on Patentability for PCT/US2011/030823, dated Oct. 11, 2012.
International Search Report and Written Opinion for PCT/US2009/059131, dated Jan. 3, 2011.
International Search Report and Written Opinion for PCT/US2011/030823, dated Nov. 25, 2011.
Jakobovits et al., "Analysis of homozygous mutant chimeric mice: Deletion of the immunoglobulin heavy-chain joining region blocks B-cell development and antibody production," Proc. Natl. Acad. Sci. (1993) 90: 2551-2555.
Janssens et al. "Generation of heavy-chain-only antibodies in mice," Proc. Natl. Acad. Sci. (2006) 103: 15130-15135.
Karreman, "A new set of positive/negative selectable markers for mammalian cells," Gene 218:57-61, 1998.
Kawasaki et al., "The Organization of the Human Immunoglobulin λ Gene Locus," Gen. Res. (1995) 5: 125-135.
Kodumal et al., "Total synthesis of long DNA sequences: Synthesis of a contiguous 32-kb polyketide synthase gene cluster," Proc. Natl. Acad. Sci. (2004), 101:15573-15578.
Lepage et al. "Rapid generation of nested chromosomal deletions on mouse chromosome 2," Proc. Natl. Acad. Sci. (2000) 97: 10471-10476.
Li et al. "Generation of mice with a 200-kb amyloid precursor protein gene deletion by Cre recombinase-mediated site-specific recombination in embryonic stem cells," Proc. Natl. Acad. Sci. (1996) 93: 6158-6162.
Lonberg, "Human antibodies from transgenic animals," Nature Biotechnology 23(9):1117-1125, 2005.
Loset et al., "Differential Segmental Flexibility and Reach Dictate the Antigen Binding Mode of Chimeric IgD and IgM: Implications for the Function of the B Cell Receptor," The Journal of Immunology 172:2925-2934, 2004.
Lutz et al., "IgD can largely substitute for loss of IgM function in B cells," Nature, (1998), 393:797-801.
Mansour et al., "Disruption of the proto-oncogene int-2 in mouse embryo-derived stem cells: a general strategy for targeting mutations to non-selectable genes," Nature 336:348-352, 1988.
Mendez et al. "Functional transplant of megabase human immunoglobulin loci recapitulates human antibody response in mice," Nature Genetics, (1997), 15(2):146-156.
Nissim, et al., "Mapping of the high affinity FeE receptor binding site to the third constant region domain of Ig E," The EMBO Journal, 10:(1):101-107 (1991).
Nitschke et al. "Immunoglobulin D-deficient mice can mount normal immune responses to thymus-independent and -dependent antigens," Proc. Natl. Acad. Sci. (1993) 90: 1887-1891.

(56) References Cited

OTHER PUBLICATIONS

Pan et al., "Regulation of the promoter for human immunoglobulin γ3 germ-line transcription and its interaction with the 3'α enhancer," Eur. J. Immunol. 30:1019-1029, 2000.
Perlot et al."Elucidation of IgH intronic enhancer functions via germ-line deletion," Proc. Natl. Acad. Sci. (2005) 97: 14362-14367.
Pruzina, et al., "Human monoclonal antibodies to HIV-1 gp 140 from mice bearing YAC-based human immunoglobulin transloci," Protein Engineering, Design & Selection, 24(10):791-799 (2011).
Puech et al."Normal cardiovascular development in mice deficient for 16 genes in 550 kb of the velocardiofacial/ DiGeorge syndrome region," Proc. Natl. Acad. Sci. (2000) 97: 10090-10095.
Ramsden and Wu, "Mouse κ light-chain recombination signal sequences mediate recombination more frequently than do those of λ light chain," Proc. Natl. Acad. Sci. (1991) 88: 10721-10725.
Ren et al. "Silencing of the immunoglobulin heavy chain locus by removal of all eight constant-region genes in a 200-kb region," Genomics (2004) 84: 686-695.
Roes and Rajewsky, "Immunoglobulin D (IgD)-deficient Mice Reveal an Auxiliary Receptor Function for IgD in Antigen-mediated Recruitment of B Cells Immunoglobulin D (IgD)-deficient Mice Reveal an Auxiliary Receptor Function for IgD in Antigen-mediated Recruitment of B Cells," J. Exp Med. (1993) 177: 45-55.
Roux et al., "Flexibility of Human IgG Subclasses," The Journal of Immunology 159:3372-3382, 1997.
Selsing et al.,"Immunoglobulin λ Genes," Acad. Press Ltd., (1989) pp. 111-122.
Shizuya and Kouros-Mehr, "The development and applications of the bacterial artificial chromosome cloning system," Keio J Med, 2001, 50(1):26-30.
Stevenson, G.T., et al., "Conjugation of human Fc gamma in closed-hinge or open-hinge configuration to Fab'gamma and analogous ligands," Journal of Immunology, 158:2242-2250 (1997).
Strachan and Read, Human Molecular Genetics, Second Edition. New York: Wiley-Liss, 1999, Chapters 21 and 22.
Tabuchi et al., "Titration of Hepatitis B Virus Infectivity in the Sera of Pre-Acute and Late Acute Phases of HBV Infection: Transmission Experiments to Chimeric Mice With Human Liver Repopulated Hepatocytes," J Med Virol., (2008), 80(12):2064-2068.
Takeda et al., "Deletion of the immunoglobulin χ chain intron enhancer abolishes χ chain gene rearrangement in cis but not λ chain gene rearrangement in trans," EMBO J. (1993) 12: 2329-2336.
Taylor et al., "A transgenic mouse that expresses a diversity of human sequence heavy and light chain immunoglobulins," Nucleic Acids Research 20(23):6287-6295, 1992.
Testa et al., "Engineering the mouse genome with bacterial artificial chromosomes to create multipurpose alleles," Nature Biotech. (2003), 21:443-447.
Thomas et al., "High Frequency Targeting of Genes to Specific Sites in the Mammalian Genome," Cell 44:419-428, 1986.
Thomas et al., "Site-Directed Mutagenesis by Gene Targeting in Mouse Embryo-Derived Stem Cells," Cell 51:503-512, 1987.
Torres, et al., "Exchanging Murine and Human Immunoglobulin Constant Chains Affects the Kinetics and Thermodynamics of Antigen Binding and Chimeric Antibody Autoreactivity," PLoS ONE, 12: 10 Pages (2007).
Torres, et al., "The Immunoglobulin Heavy Chain Constant Region Affects Kinetic and Thermodynamic Parameters of Antibody Variable Region Interaction with Antigen," Journal of Biological Chemistry, 282(18):13917-13927 (2007).
Valenzuela et al., "High-through put engineering of the mouse genome coupled with high-resolution expression analysis," Nature Biotech. (2003), 21:652-659.
Venken et al., "P[acman]: A BAC Transgenic Platform for Targeted Insertion of Large DNA Fragments in *D. melanogaster*," Science 314:1747-1751, 2006.
Wu et al., "Double replacement: Strategy for efficient introduction of subtle mutations into the murine Colla-1 gene by homologous recombination in embryonic stem cells," Proc. Natl. Acad. Sci. USA 91:2819-2823, 1994.
Yang and Seed, "Site-specific gene targeting in mouse embryonic stem cells with intact bacterial artificial chromosomes," Nature Biotech. (2003), 21:447-451.
Zhang et al., "DNA cloning by homologous recombination in *Escherichia coli*," Nature Biotechnology 18:1314-1317, 2000.
Zheng et al., "Engineering Mouse Chromosomes with Cre-IoxP: Range, Efficiency, and Somatic Applications" Molec. Cell. Biol. (2000) 20: 648-655.
Zhu et al., "Genomic interval engineering of mice identifies a novel modulator of triglyceride production" Proc. Natl. Acad. Sci. (2000) 97: 1137-1142.
Zou et al., "Block in Development at the Pre-B-II to Immature B Cell Stage in Mice Without Ig and Igλ Light Chain[1]," J. Immunol. (2003) 170: 1354-1361.
Zou et al., "Gene targeting in the Igχ locus: efficient generation of λ chain-expressing B cells, independent of gene rearrangements in Igχ" EMBO J. (1993) 12: 811-820.
Barthold, "Genetically altered mice: phenotypes, no phenotypes, and Faux phenotypes," Genetica, 122:75-88 (2004).
Garcia-Arocena, The Jackson Laboratory, "Same Mutation, Different Phenotype?", (2014) (5 pages).
Grunberg, et al., "High-yield production of recombinant antibody fragments in HEK-293 cells using sodium butyrate," BioTechniques, 34(5):968-972 (2003).
Heiman-Patterson, et al., "Effect of genetic background on phenotype variability in transgenic mouse models of amyotrophic lateral sclerosis: a window of opportunity in the search for genetic modifiers," Amyotrophic Lateral Schlerosis, 12:79-86 (2011).
Murphy, "VelocImmune: Immunoglobulin Variable Region Humanized Mice," Chapter 8, Recombinant Antibodies for Immunotherapy, ed. Melyn Little, Affirmed Therapeutics, Cambridge University Press(10 pages) 2009.
Popov, et al., "A human immunoglobulin lambda locus is similarly well expressed in mice and humans," Journal of Experimental Medicine, 189(10):1611-1619 (1999).
Stevens, et al., "Human Antibody Discovery, VelocImmune-A novel platform," Pharma Focus Asia, 8:72-74 (2008).

\* cited by examiner

GENETIC ENGINEERING OF NON-HUMAN ANIMALS FOR THE PRODUCTION OF CHIMERIC ANTIBODIES

CROSS-REFERENCE TO RELATED APPLICATION

This application is a divisional of U.S. application Ser. No. 15/408,114 filed on Jan. 17, 2017, which is a divisional of U.S. application Ser. No. 13/638,522 filed on Mar. 5, 2013 now U.S. Pat. No. 9,580,491 issued on Feb. 28, 2017, which is a 317 National Phase Application of PCT/US2011/030823 filed on Mar. 31, 2011, which claims the benefit under 35 U.S.C. § 119(e) of U.S. Provisional Patent Application No. 61/319,690 filed Mar. 31, 2010 and U.S. Provisional Patent Application No. 61/361,302 filed Jul. 2, 2010. The content of each of these patent applications is incorporated by reference in its entirety.

BACKGROUND

Technical Field

The present invention is directed generally to chimeric immunoglobulin chains, antibodies and non-human animals and cells, and the production thereof.

Description of the Related Art

Disease therapies utilizing monoclonal antibodies (mAbs) have revolutionized medicine, and mAb-based drugs are now utilized in the treatment of cancer, autoimmunity, inflammation, macular degeneration, infections, etc. However, the available technologies for generation and discovery of mAbs for use in the prevention and treatment of diseases and disorders have significant drawbacks including inefficiency, absence or loss of sufficient potency, absence or loss of specificity and the induction of an immune response against the therapeutic mAb. The first attempts to use mAbs as therapeutics were hindered by the immunogenicity of the mouse amino acid composition of the mAbs. When administered to humans, the mouse amino acid sequence elicited a human anti-mouse antibody (HAMA) response that dramatically reduced the potency and pharmacokinetics of the drug as well as causing severe and potentially fatal allergic reactions.

Additional methods to generate mAb therapeutics include chimerized mAbs (cmAbs) created through recombinant DNA technology combining a mouse-derived variable domain appended to a human constant region. Other methods of generating antibodies involve humanizing mAbs in vitro to further reduce the amount of mouse amino acid sequence in a therapeutic mAb. Antibody-display technologies developed to generate "fully-human" antibodies in vitro have yet to adequately mimic the natural antibody maturation process that occurs during an in vivo immune response (see pg. 1122-23, Lonberg, *Nat. Biotech.* (2005) 23:1117-1125.) mAbs developed using these methods can elicit an immune response that can reduce efficacy and/or be life-threatening, and these processes are typically time-consuming and costly. Also, during the molecular processes inherent in these methods, loss of affinity and epitope shifting can occur, thereby reducing potency and introducing undesirable changes in specificity.

Transgenic mice have been engineered to produce fully human antibodies by introducing human antibody transgenes to functionally replace inactivated mouse immunoglobulin (Ig) loci. However, many of these transgenic mouse models lack important components in the antibody development process, such as sufficient diversity in the genes from which antibody variable regions are generated, the ability to make IgD (Loset et al., *J. Immunol.*, (2004) 172:2925-2934), important cis regulatory elements important for class switch recombination (CSR), or a fully functional 3' locus control region (LCR) (e.g., U.S. Pat. No. 7,049,426; and Pan et al., *Eur. J. Immunol.* (2000) 30:1019-1029). Some transgenic mice contain yeast artificial chromosomes or human miniloci as integrated transgenes. Others carry transchromosomes that exhibit various frequencies of mitotic and meiotic instability. Furthermore, the fully human constant regions of these transgenic mice function sub-optimally due to reduced activity in conjunction with other endogenous and trans-acting components as compared to wild-type mice, e.g., the BCR signal transduction apparatus, (Igα and Igβ) and Fc receptors (FcR), respectively.

Knock-in mice have also been genetically engineered to produce chimeric antibodies that are composed of human V domains appended to mouse C domains that remain fully intact, with the fully-intact portions comprising all genomic DNA downstream of the J gene cluster (see U.S. Pat. Nos. 5,770,429 and 6,596,541 and U.S. Patent Application Publication No. 2007/0061900). Human V regions from these mice can be recovered and appended to human constant region genes by molecular biological methods and expressed by recombinant methods to produce fully-human antibodies. The antibodies from these mice may exhibit reduction or loss of activity, potency, solubility etc. when the human V region is removed from the context of the mouse C domains with which it was evolved and then appended to a human C region to make a fully human antibody. Furthermore, because of the unique and differing structures of the mouse immunoglobulin lambda locus versus that of the human immunoglobulin lambda locus and because the endogenous 3' enhancer of the mouse lambda locus may be defective, the described knock-in approach would be expected to yield an inefficiently functioning lambda locus.

Methods of transgene DNA construction for introduction into eukaryotic, particularly metazoan, species have employed DNA isolated from genomic libraries made from isolated natural DNA. Engineering of the cloned natural DNA into the final desired design for a transgene is typically achieved through processes of recombination that are cumbersome, inefficient, slow and error-prone and constrained by the availability of the DNAs present in genomic libraries. In some instances, it is desirous to construct a transgene from an organism, strain or specific haplotype thereof for which a genomic library is not readily available but for which either partial genomic sequence or transcriptome sequence information is available. These hindrances prevent the creation of transgenes comprising complexly reconfigured sequences and/or transgenes designed to comprise chimeric DNA sequence from different species or different strains or different haplotypes of the same species. As a consequence, the engineering of highly-tailored transgenes for eukaryotes, particularly metazoans, is prevented.

Current methods of developing a therapeutic mAb can alter functions of the antibody, such as solubility, potency and antigen specificity, which were selected for during initial stages development. In addition, mAbs generated by current methods have the potential to elicit a dangerous immune response upon administration. Current human and chimeric antibody producing mice lack appropriate genetic content to function properly, e.g., genetic diversity, cis regulatory elements, trans acting regulatory elements, signaling domains, genetic stability. It would be beneficial to develop methods and compositions for the enhanced generation and discovery of therapeutic antibodies and that retain potency and specificity through the antibody generation, discovery, development, and production process without eliciting an immune response, as well as methods of producing such antibodies. Some of the transgene compositions comprise DNA sequences so complexly modified that construction of these improvements and derivation of products therefrom have been prevented. While mice are preferred because of their economy and established utility, a broad solution across multiple species is desirable. The present invention provides a solution for making and introducing such transgenes, improving the genetic background into which these transgenes would function if deployed in a mouse, and, in particular instances, generating improved antibodies in transgenic animals.

BRIEF SUMMARY

The present invention relates to non-human animals and cells, transgenes, antibodies, methods, compositions, including pharmaceutical compositions, as well as kits of various embodiments disclosed herein. More specifically, the present invention relates to methods, compositions and kits relating to chimeric Ig chains and antibodies produced by the non-human animals and cells and the human antibodies and fragments thereof engineered from the variable domains of said chimeric antibodies. In certain embodiments of the invention, the non-human animals are mammals.

One embodiment of the invention relates to a method of producing a cell comprising a genome that comprises a chimeric immunoglobulin chain, wherein the immunoglobulin chain comprises a non-endogenous variable domain and a chimeric constant region, comprising the steps of (1) designing a DNA construct in silico, wherein said construct comprises one or more non-endogenous V, (D) and/or J gene segments and one or more non-endogenous constant region gene segments; (2) producing said DNA construct; and (3) introducing the construct into the genome of a cell. In certain embodiments, the non-endogenous variable domain is human. In another embodiment, the chimeric constant region comprises a mouse constant domain gene segment. In one embodiment, the chimeric constant region is encoded by a non-endogenous polynucleotide sequence derived from two or more non-endogenous species, alleles and/or haplotypes. In yet another embodiment, the non-endogenous variable domain is encoded by a polynucleotide sequence derived from two or more species, alleles and/or haplotypes. In certain embodiments, the chimeric immunoglobulin chain is a light chain.

In certain other embodiments, the chimeric immunoglobulin chain is a heavy chain. In a related embodiment, the chimeric constant region comprises a non-endogenous CH1 domain. In another related embodiment, the method further comprises the steps of designing a second DNA construct in silico, wherein said construct comprises a non-endogenous immunoglobulin light chain; producing said second DNA construct; and introducing the second construct into the genome of a cell. In one embodiment, the non-endogenous light chain comprises one or more human Vκ gene segments. In another embodiment, the non-endogenous light chain further comprises one or more human Jκ and Cκ gene segments. In yet another embodiment, the non-endogenous light chain comprises 8 or more human Vλ gene segments. In a related embodiment, the non-endogenous light chain further comprises 7 or more human Jλ-Cλ gene segment pairs.

One embodiment relates to a non-human cell comprising a genome that comprises a chimeric immunoglobulin chain, wherein the immunoglobulin chain comprises a non-endogenous variable domain and a chimeric constant region, wherein the cell is produced by a method comprising the steps of (1) designing a DNA construct in silico, wherein said construct comprises one or more non-endogenous V, (D) and/or J gene segments and one or more non-endogenous constant region gene segments; (2) producing said DNA construct; and (3) introducing the construct into the genome of a cell. Another embodiment encompasses a non-human animal generated from the cell. Another embodiment provides a chimeric immunoglobulin heavy chain produced by the non-human animal. Certain embodiments provide a chimeric antibody produced by the non-human animal.

Another embodiment of the invention provides a chimeric immunoglobulin heavy chain comprising a non-endogenous variable domain and a chimeric constant region, wherein the non-endogenous variable domain is derived from a non-human animal. In a related embodiment, the chimeric constant region comprises a non-endogenous CH1 domain. One embodiment provides a chimeric immunoglobulin heavy chain comprising a non-endogenous variable domain and a chimeric constant region, wherein the chimeric constant region is encoded by a non-endogenous polynucleotide sequence derived from two or more non-endogenous species, alleles and/or haplotypes. Another embodiment provides a chimeric immunoglobulin heavy chain comprising a non-endogenous variable domain and a chimeric constant region, wherein said non-endogenous variable domain is encoded by a polynucleotide sequence derived from two or more species, alleles and/or haplotypes.

Yet another embodiment is directed to a polynucleotide encoding the disclosed chimeric immunoglobulin heavy chain. In particular embodiments, the polynucleotide comprises coding and non-coding sequences. In certain embodiments, the polynucleotide is synthetic. One embodiment relates to a construct comprising the polynucleotide a polynucleotide encoding the disclosed chimeric immunoglobulin heavy chain.

Another embodiment of the invention provides a chimeric antibody, or an antigen-binding fragment thereof, comprising (1) a chimeric immunoglobulin heavy chain, wherein the chimeric heavy chain comprises a non-endogenous heavy chain variable domain and a chimeric heavy chain constant region, and (2) a non-endogenous immunoglobulin light chain, wherein the chimeric heavy chain constant region is derived from two or more non-endogenous species, alleles and/or haplotypes. Yet another embodiment provides a chimeric antibody, or an antigen-binding fragment thereof, comprising (1) a chimeric immunoglobulin heavy chain, wherein the chimeric heavy chain comprises a non-endogenous heavy chain variable domain and a chimeric heavy chain constant region, and (2) a non-endogenous immunoglobulin light chain, and wherein said non-endogenous heavy chain variable domain is derived from two or more species, alleles and/or haplotypes. One embodiment relates to a chimeric antibody, or an antigen-binding fragment thereof, comprising a chimeric immunoglobulin heavy chain, wherein the chimeric heavy chain comprises a non-endogenous variable domain and a chimeric constant region, and wherein the variable domain is derived from a non-human animal. In a related embodiment, the disclosed chimeric antibody, or antigen-binding fragment thereof, further comprises a non-endogenous light chain.

One embodiment of the invention provides a non-human cell comprising a genome that comprises a chimeric immunoglobulin heavy chain comprising a non-endogenous variable domain and a chimeric constant region, wherein the non-endogenous variable domain is derived from a non-human animal. In a related embodiment, the genome of the cell further comprises a non-endogenous immunoglobulin light chain. In particular embodiments, the genome of the cell comprises a non-endogenous Igκ light chain and a non-endogenous Igλ light chain. In certain embodiments, the cell comprises an inactivated endogenous immunoglobulin locus. One embodiment provides a chimeric antibody produced by the disclosed cell.

Yet another embodiment provides a non-human cell comprising a genome that comprises a chimeric immunoglobulin heavy chain comprising a non-endogenous variable domain and a chimeric constant region, wherein the constant region is derived from two or more non-endogenous species, alleles and/or haplotypes. One embodiment provides a non-human cell comprising a genome that comprises a chimeric immunoglobulin heavy chain comprising a non-endogenous variable domain and a chimeric constant region, wherein the non-endogenous variable domain is derived from two or more species, alleles and/or haplotypes. Another embodiment provides a non-human cell comprising a genome that comprises a synthetic transgene encoding a chimeric antibody, or an antigen-binding fragment thereof, comprising (1) a chimeric immunoglobulin heavy chain, wherein said chimeric heavy chain comprises a non-endogenous heavy chain variable domain and a chimeric heavy chain constant region. In certain embodiments, the genome of the disclosed cell further comprises a non-endogenous immunoglobulin light chain. In one embodiment, the genome of the cell comprises a non-endogenous Igκ light chain and a non-endogenous Igλ light chain. In particular embodiments, the cell comprises an inactivated endogenous immunoglobulin locus. Another embodiment provides for a chimeric antibody produced by the cell.

Another embodiment of the invention relates to a non-human animal comprising a genome that comprises a chimeric immunoglobulin heavy chain comprising a non-endogenous variable domain and a chimeric constant region, wherein the non-endogenous variable domain is derived from a non-human animal. In a related embodiment, the genome of the animal further comprises a polynucleotide sequence encoding a non-endogenous immunoglobulin light chain. In certain embodiments, the genome of the animal comprises a non-endogenous Igκ light chain and a non-endogenous Igλ light chain. In another embodiment, the animal comprises an inactivated endogenous immunoglobulin locus. In certain embodiments, the animal is a mouse. Another embodiment provides a chimeric antibody produced by the non-human animal.

Yet another embodiment of the invention provides a non-human animal comprising a genome that comprises (1) a chimeric immunoglobulin heavy chain, wherein the chimeric heavy chain comprises a non-endogenous heavy chain variable domain and a chimeric heavy chain constant region, and (2) a non-endogenous immunoglobulin light chain, wherein the chimeric heavy chain constant region is derived from two or more non-endogenous species, alleles and/or haplotypes. Another embodiment provides a non-human animal comprising a genome that comprises (1) a chimeric immunoglobulin heavy chain, wherein the chimeric heavy chain comprises a non-endogenous heavy chain variable domain and a chimeric heavy chain constant region, and (2) a non-endogenous immunoglobulin light chain, wherein the non-endogenous heavy chain variable domain is derived from two or more species, alleles and/or haplotypes. One embodiment provides a non-human animal comprising a genome that comprises a synthetic transgene encoding a chimeric antibody, or an antigen-binding fragment thereof, comprising (1) a chimeric immunoglobulin heavy chain, wherein the chimeric heavy chain comprises a non-endogenous heavy chain variable domain and a chimeric heavy chain constant region. In particular embodiments, the genome further comprises a non-endogenous immunoglobulin light chain. In certain embodiments, the genome of the animal comprises a non-endogenous Igκ light chain and a non-endogenous Igλ light chain. In particular embodiments, the cell comprises an inactivated endogenous immunoglobulin locus. Another embodiment provides a chimeric antibody produced by the disclosed animal.

One embodiment of the invention provides a non-human animal comprising an inactivated endogenous Ig locus, wherein the endogenous Ig locus comprises a deletion that impairs formation of a functional variable domain and formation of a constant region capable of driving primary B cell development. In certain embodiments, the endogenous immunoglobulin locus is a heavy chain locus. In certain other embodiments, the endogenous immunoglobulin locus is a light chain locus. Another embodiment provides a non-human cell comprising an inactivated endogenous Ig locus, wherein the endogenous Ig locus comprises a deletion that impairs formation of a functional variable domain and formation of a constant region capable of driving primary B cell development.

One embodiment provides a DNA construct comprising a first flanking sequence, a transgene, and a second flanking sequence, wherein the transgene comprises a polynucleotide sequence capable of introducing a deletion in an endogenous Ig locus that impairs formation of a functional variable domain and formation of a constant region capable of supporting primary B cell development. Another embodiment provides a kit comprising the DNA construct. Another embodiment provides a method for inactivating an endogenous immunoglobulin locus comprising impairing the formation of a functional variable domain, and impairing the formation of a constant region capable of driving primary B cell development.

Another embodiment of the invention provides a method of producing an antibody display library comprising providing a non-human animal having a genome that comprises a chimeric immunoglobulin heavy chain, wherein the chimeric heavy chain comprises a non-endogenous heavy chain variable domain and a chimeric heavy chain constant region; recovering polynucleotide sequences from the animal, wherein the polynucleotide sequences encode immunoglobulin light chain variable regions and non-endogenous immunoglobulin heavy chain variable regions; and producing an antibody display library comprising the heavy chain and light chain variable regions. One embodiment of the invention provides an antibody display library comprising immunoglobulin heavy chain variable regions generated by a non-human animal having a genome that comprises a chimeric immunoglobulin heavy chain, wherein the chimeric heavy chain comprises a non-endogenous heavy chain variable domain and a chimeric heavy chain constant region, wherein the variable regions are derived from chimeric antibodies.

DETAILED DESCRIPTION

Overview

Figure 1:
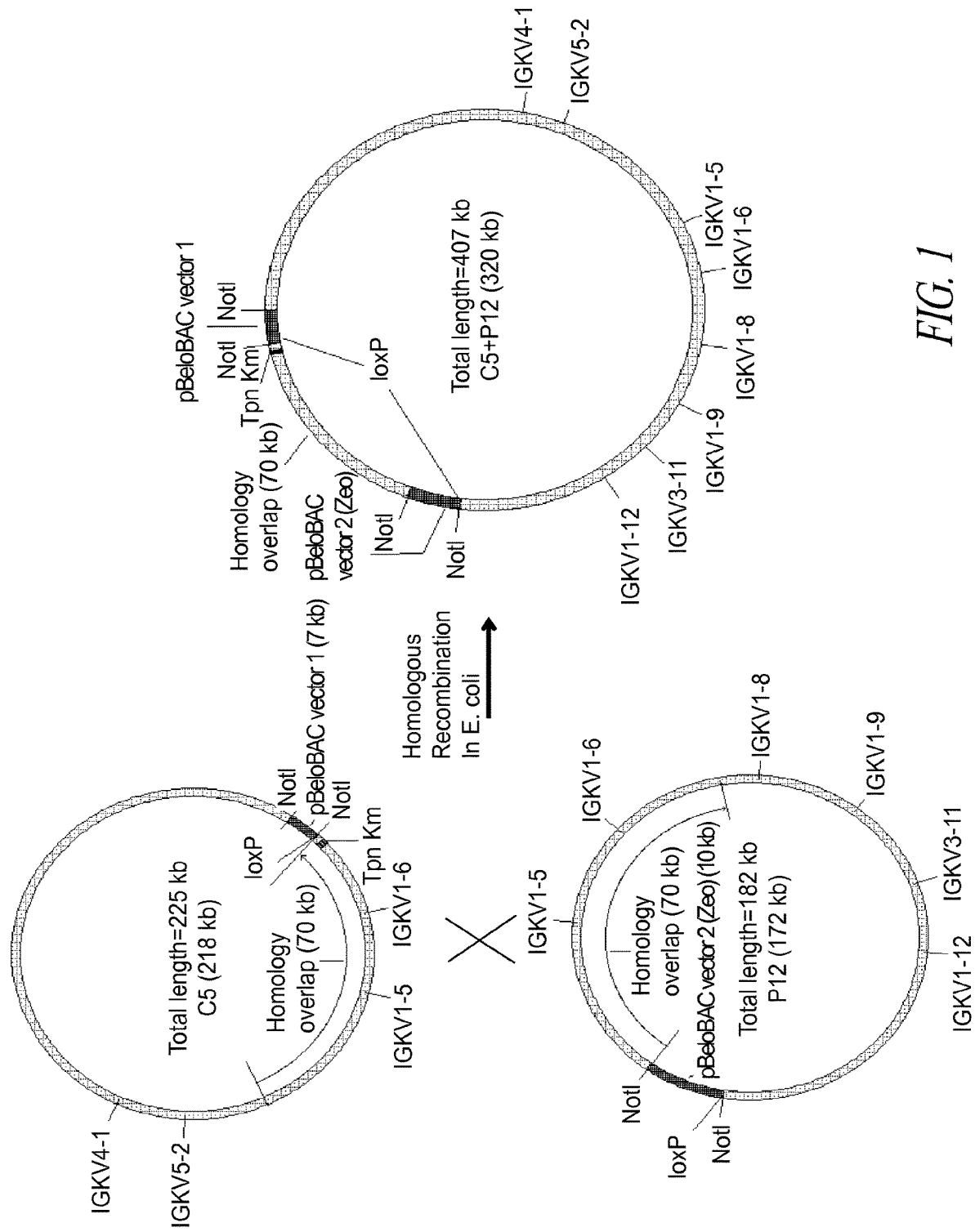
FIG. 1 depicts homologous recombination of BAC C5 and BAC P12 in *E. coli*.

The present invention includes chimeric antibodies, non-human animals that produce chimeric or humanized antibodies, methods of producing such non-human cells and animals, and compositions and kits comprising the antibodies. In specific embodiments of the invention, the non-human animals are mammals.

Chimeric antibodies, and antigen-binding fragments thereof, described herein comprise a non-endogenous variable domain and a chimeric heavy chain constant region. In particular embodiments, an IgH chain comprises one or more non-endogenous V, D and J gene segments, a non-endogenous CH1 domain, and endogenous CH2 and CH3 domains. In certain embodiments, an antibody, or antigen-binding fragment thereof, comprising the chimeric IgH chain described herein further comprises an IgL chain having an amino acid sequence encoded for by a non-endogenous nucleotide sequence. In other embodiments, an antibody, or antigen-binding fragment thereof, comprising the chimeric IgH chain described herein further comprises an IgL chain having an amino acid sequence encoded for by endogenous and non-endogenous nucleotide sequences.

Engineering the chimeric antibodies in this manner prevents alteration in the V domain conformation resulting from the in vitro switch from a first C region, particularly a CH1 domain and optionally a portion of the hinge region from one species, e.g., mouse, with which it was evolved during the in vivo immune response to a second C region, particularly a CH1 domain and optionally a portion of the hinge region from another species, e.g., human. The antibodies produced by the animals of the present invention do not exhibit the reduction or loss of activity and potency seen in antibodies from other chimeric antibody producing animals when, for example, the human V region is appended to a human C region to make a fully human antibody, which may be caused by altered conformation of the VH domain resulting from the changing of the CH1 domain and/or by differences in antigen binding because of changed length or flexibility of the upper hinge regions (the peptide sequence from the end of the CH1 to the first cysteine residue in the hinge that forms an inter-heavy chain disulfide bond, and which are variable in length and composition) when switching from mouse to human constant region (Roux et al., *J. Immunology* (1997) 159:3372-3382 and references therein). The middle hinge region is bounded by the cysteine residues that form inter-heavy chain disulfide bonds.

Definitions

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems. As used in the present disclosure and claims, the singular forms "a," "an," and "the" include plural forms unless the context clearly dictates otherwise.

As used herein, "antibody" and "immunoglobulin" (Ig) are used interchangeably herein and refer to protein molecules produced by B cells that recognize and bind specific antigens and that may either be membrane bound or secreted. Antibodies may be monoclonal, in that they are produced by a single clone of B cells and therefore recognize the same epitope and have the same nucleic acid and amino acid sequence, or polyclonal, in that they are produced by multiple clones of B cells, recognize one or more epitopes of the same antigen and typically have different nucleic acid and amino acid sequences.

Antibody, or Ig, molecules are typically comprised of two identical heavy chains and two identical light chains linked together through disulfide bonds. There are two types of IgL, Igκ and Igλ. Both heavy chains (IgH) and light chains (IgL) contain a variable (V) region or domain and a constant (C) region or domain. The portion of the IgH locus encoding the V region comprises multiple copies of variable (V), diversity (D), and joining (J) gene segments. The portion of the IgL loci, Igκ and Igλ, encoding the V region comprises multiple copies of V and J gene segments. The V region encoding portion of the IgH and IgL loci undergo gene rearrangement, e.g., different combinations of gene segments arrange to form the IgH and IgL variable regions, to develop diverse antigen specificity in antibodies. The secreted form of the IgH C region is made up of three C domains, CH1, CH2, CH3, optionally CH4 (Cμ), and a hinge region. The membrane-bound form of the IgH C region also has membrane and intra-cellular domains. The IgH constant region determines the isotype of the antibody, e.g. IgM, IgD, IgG1, IgG2, IgG3, IgG4, IgA and IgE in humans. It will be appreciated that non-human mammals encoding multiple Ig isotypes will be able to undergo isotype class switching.

A "Fab" domain or fragment comprises the N-terminal portion of the IgH, which includes the V region and the CH1 domain of the IgH, and the entire IgL. A "F(ab')$_2$" domain comprises the Fab domain and a portion of the hinge region, wherein the 2 IgH are linked together via disulfide linkage in the middle hinge region. Both the Fab and F(ab')$_2$ are "antigen-binding fragments." The C-terminal portion of the IgH, comprising the CH2 and CH3 domains, is the "Fc" domain. The Fc domain is the portion of the Ig recognized by cell receptors, such as the FcR, and to which the complement-activating protein, C1q, binds. The lower hinge region, which is encoded in the 5' portion of the CH2 exon, provides flexibility within the antibody for binding to FcR receptors.

As used herein "chimeric antibody" refers to an antibody encoded by a polynucleotide sequence containing polynucleotide sequences derived from two or more species.

A "humanized" antibody is a chimeric antibody that has been engineered so as to comprise more human sequence than its parental molecule. Humanized antibodies are less immunogenic after administration to humans when compared to non-humanized antibodies prepared from another species. For example, a humanized antibody may comprise the variable region of a chimeric antibody appended to a human constant region. Chimeric antibodies described herein can be used to produce a fully human antibody.

As used herein "chimeric Ig chain" refers to an Ig heavy chain or an Ig light chain encoded by a polynucleotide sequence containing polynucleotide sequences derived from two or more species. For example, a chimeric Ig heavy chain may comprise human VH, DH, JH, and CH1 gene segments and mouse CH2 and CH3 gene segments.

"Polypeptide," "peptide" or "protein" are used interchangeably to describe a chain of amino acids that are linked together by chemical bonds. A polypeptide or protein may be an IgH, IgL, V domain, C domain, or an antibody.

"Polynucleotide" refers to a chain of nucleic acids that are linked together by chemical bonds. Polynucleotides include, but are not limited to, DNA, cDNA, RNA, mRNA, and gene sequences and segments. Polynucleotides may be isolated from a living source such as a eukaryotic cell, prokaryotic cell or virus, or may be derived through in vitro manipulation by using standard techniques of molecular biology, or by DNA synthesis, or by a combination of a number of techniques.

"Locus" refers to a location on a chromosome that comprises one or more genes or exons, such as an IgH or Igκ locus, the cis regulatory elements, and the binding regions to which trans-acting factors bind. As used herein, "gene" or "gene segment" refers to the polynucleotide sequence encoding a specific polypeptide or portion thereof, such as a VL domain, a CH1 domain, an upper hinge region, or a portion thereof. As used herein, "gene segment" and "exon" may be used interchangeably and refer to a polynucleotide encoding a peptide, or a portion thereof. A gene, or gene segment, may further comprise one or more introns, transcriptional control elements, e.g., promoters, enhancers, or other non-coding regions (e.g., cis regulatory elements, e.g., 5' and/or 3' untranslated regions, poly-adenylation sites).

As used herein, the term "inactivated Ig locus" refers to an Ig locus that does not encode a functional Ig chain. A "functional variable region" produce from an Ig locus refers to a polynucleotide sequence capable of undergoing V-(D)-J recombination, being transcribed and said transcript being translated into a variable region polypeptide that is capable of being expressed on a cell surface. A "functional heavy chain constant region" refers to a constant region capable of being operationally joined to a variable region and driving primary B cell development. Primary B cell development refers to the development of B cells in the primary lymphoid organs, e.g., bone marrow, and encompasses the transition from stem cell to immature B cell, including the developmental stages of early pro-B cell (i.e., IgH D-J rearranging), late pro-B cell (i.e., IgH V-DJ rearranging), large pre-B cell (i.e., expresses pre-B receptor), and small pre-B cell (i.e., IgL V-J rearranging). By "driving" primary B cell development, it is meant that the functional heavy chain constant region is capable of, e.g., anchoring to the cell membrane, signal transduction, and/or binding an Fc receptor. A "functional light chain constant region" refers to a constant region capable of being operationally joined to a variable region and binding to heavy chain to advance B cell development beyond the small pre-B cell stage.

"Impair" refers to the introduction of a deletion or mutation that results in, e.g., a variable region that is no longer functional or a constant region that is no longer function. For example, homozygous deletion of Cμ impairs an IgH from driving primary B cell development in some mammals and strains thereof.

"Mutation" refers to a change in a naturally occurring polynucleotide or polypeptide sequence. A mutation may result in a functional change. Mutations include both the addition of nucleotides and the deletion of nucleotides. "Deletion" refers to the removal of one or more nucleotides from the naturally occurring endogenous polynucleotide sequence. Deletions and additions may introduce a frameshift mutation. Deletions may also remove entire genes, gene segments or modules. In some instances, a deletion of part of the naturally occurring endogenous sequence may coincide with the addition of a non-endogenous sequence. For example, a portion of the endogenous polynucleotide sequence may be removed, i.e., deleted, upon homologous recombination with a polynucleotide comprising a non-endogenous sequence, e.g., a selection marker. In other aspects, a deletion of an endogenous polynucleotide sequence may occur after the introduction of two non-endogenous recognition sequence for a site-specific recombinase, e.g., a loxP site, followed by exposure to the recombinase, e.g., CRE.

The term "endogenous" refers to a polynucleotide sequence which occurs naturally within the cell or animal. "Orthologous" refers to a polynucleotide sequence that encodes the corresponding polypeptide in another species, e.g., a human CH1 domain and a mouse CH1 domain. The term "syngeneic" refers to a polynucleotide sequence that is found within the same species that may be introduced into an animal of that same species, e.g., a mouse Vκ gene segment introduced into a mouse. It should be noted that the polynucleotide sequence from two individuals of the same species but of different strains may have regions of significant difference.

As used herein, the term "homologous" or "homologous sequence" refers to a polynucleotide sequence that has a highly similar sequence, or high percent identity (e.g. 30%, 40%, 50%, 60%, 70%, 80%, 90% or more), to another polynucleotide sequence or segment thereof. For example, a DNA construct of the invention may comprise a sequence that is homologous to a portion of an endogenous DNA sequence to facilitate recombination at that specific location. Homologous recombination may take place in prokaryotic and eukaryotic cells.

As used herein, "flanking sequence" or "flanking DNA sequence" refers to a DNA sequence adjacent to a non-endogenous DNA sequence in a DNA construct that is homologous to an endogenous DNA sequence or a previously recombined non-endogenous sequence, or a portion thereof. DNA constructs of the invention may have one or more flanking sequences, e.g., a flanking sequence on the 3' and 5' end of the non-endogenous sequence or a flanking sequence on the 3' or the 5' end of the non-endogenous sequence. The flanking sequence may be homologous to an endogenous sequence within an endogenous gene, or the flanking sequence may be homologous to an endogenous sequence adjacent to (i.e., outside of) an endogenous gene.

The phrase "homologous recombination-competent cell" refers to a cell that is capable of homologously recombining DNA fragments that contain regions of overlapping homology. Examples of homologous recombination-competent cells include, but are not limited to, induced pluripotent stem cells, hematopoietic stem cells, bacteria, yeast, various cell lines and embryonic stem (ES) cells.

A "non-human animal" refers to any animal other than a human such as, e.g., avians, reptiles and mammals. "Non-human mammal" refers to an animal other than humans which belongs to the class Mammalia. Examples of non-human mammals include, but are not limited to, non-human primates, camelids, rodents, bovines, ovines, equines, dogs, cats, goats, sheep, dolphins, bats, rabbits, and marsupials. Preferred non-human mammals rely primarily on somatic hypermutation and/or gene conversion to generate antibody diversity, e.g., mouse, rabbit, pig, sheep, goat, camelids, rodents and cow. Particularly preferred non-human mammals are mice.

The term "transgenic" refers to a cell or animal comprising a non-endogenous polynucleotide sequence, e.g., a transgene derived from another species, incorporated into its genome. For example, a mouse which contains a human VH gene segment integrated into its genome outside the endogenous mouse IgH locus is a transgenic mouse; and a mouse which contains a human VH gene segment integrated into its genome directly replacing an endogenous mouse VH in the endogenous mouse IgH locus is a transgenic mouse, sometimes also referred to as a "knock-in" mouse. In transgenic cells and non-human mammals, the non-endogenous polynucleotide sequence may either be expressed with the endogenous gene, ectopically in the absence of the endogenous gene or in the absence of the corresponding, or orthologous, endogenous sequence originally found in the cell or non-human mammal.

As used herein, "replace" refers to both direct and functional replacement. By "direct replacement" it is meant that an endogenous DNA sequence is replaced with an engineered DNA sequence that comprises a non-endogenous sequence at the location of the endogenous sequence in the genome, such as by homologous recombination. For example, the endogenous DNA sequence is removed via homologous recombination, or the endogenous sequence remaining between two incorporated non-endogenous sequences is deleted. By "functional replacement" it is meant that the function (e.g., as performed by the polypeptide produced from the engineered DNA sequence) of an endogenous DNA sequence is carried out by a non-endogenous DNA sequence. For example, an endogenous IgH locus can be functionally replaced by a transgene that encodes a chimeric IgH chain and that is inserted into the genome outside of the endogenous IgH locus.

A "humanized" animal, as used herein refers to a non-human animal, e.g., a mouse, that has a composite genetic structure that retains gene sequences of the non-human animal, in addition to one or more gene segments and or gene regulatory sequences of the original genetic makeup having been replaced with analogous human sequences.

As used herein, the term "vector" refers to a nucleic acid molecule into which another nucleic acid fragment can be integrated without loss of the vector's ability to replicate. Vectors may originate from a virus, a plasmid or the cell of a higher organism. Vectors are utilized to introduce foreign or recombinant DNA into a host cell, wherein the vector is replicated.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes an RNA, for expressing the encoded RNA in a particular cell, either for subsequent translation of the RNA into a polypeptide or for subsequent trans regulatory activity by the RNA in the cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, alpha virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb* 25:37-42, 1993; Kirshenbaum et al., *J. Clin. Invest* 92:381-387, 1993; each of which is incorporated herein by reference).

A DNA vector utilized in the methods of the invention can contain positive and negative selection markers. Positive and negative markers can be genes that when expressed confer drug resistance to cells expressing these genes. Suitable selection markers for *E. coli* can include, but are not limited to: Km (Kanamycin resistant gene), tetA (tetracycline resistant gene) and beta-lactamase (ampicillin resistant gene). Suitable selection markers for mammalian cells in culture can include, but are not limited to: hyg (hygromycin resistance gene), puro (puromycin resistance gene) and G418 (neomycin resistance gene). The selection markers also can be metabolic genes that can convert a substance into a toxic substance. For example, the gene thymidine kinase when expressed converts the drug gancyclovir into a toxic product. Thus, treatment of cells with gancylcovir can negatively select for genes that do not express thymidine kinase.

In a related aspect, the selection markers can be "screenable markers," such as green fluorescent protein (GFP), yellow fluorescent protein (YFP), red fluorescent protein (RFP), GFP-like proteins, and luciferase.

Various types of vectors are available in the art and include, but are not limited to, bacterial, viral, and yeast vectors. A DNA vector can be any suitable DNA vector, including a plasmid, cosmid, bacteriophage, p1-derived artificial chromosome (PAC), bacterial artificial chromosome (BAC), yeast artificial chromosome (YAC), or mammalian artificial chromosome (MAC). In certain embodiments, the DNA vector is a BAC. The various DNA vectors are selected as appropriate for the size of DNA inserted in the construct. In one embodiment, the DNA constructs are bacterial artificial chromosomes or fragments thereof.

The term "bacterial artificial chromosome" or "BAC" as used herein refers to a bacterial DNA vector. BACs, such as those derived from *E. coli*, may be utilized for introducing, deleting or replacing DNA sequences of non-human mammalian cells or animals via homologous recombination. *E. coli* can maintain complex genomic DNA as large as 500 kb or greater in the form of BACs (see Shizuya and Kouros-Mehr, Keio *J Med.* 2001, 50(1):26-30), with greater DNA stability than cosmids or yeast artificial chromosomes. In addition, BAC libraries of human DNA genomic DNA have more complete and accurate representation of the human genome than libraries in cosmids or yeast artificial chromosomes. BACs are described in further detail in U.S. application Ser. No. 10/659,034 and 61/012,701, which are hereby incorporated by reference in their entireties.

DNA fragments comprising an Ig locus, or a portion thereof, to be incorporated into the non-human mammal are isolated from the same species of non-human mammal prior to humanization of the locus. Multiple BACs containing overlapping fragments of an Ig locus can be humanized and the overlapping fragments recombine to generate a continuous IgH or IgL locus. The resulting chimeric Ig locus comprises the human gene segments operably linked to the non-human mammal Ig gene segments to produce a functional Ig locus, wherein the locus is capable of undergoing gene rearrangement and thereby producing a diversified repertoire of chimeric antibodies.

These processes for recombining BACs and/or of engineering a chimeric Ig locus or fragment thereof requires that a bacterial cell, such as *E. coli*, be transformed with a BAC containing the host Ig locus or a portion thereof. The BAC containing bacillus is then transformed with a recombination vector comprising the desired human Ig gene segment linked to flanking homology sequence shared with the BAC containing the host Ig locus or portion thereof. The shared sequence homology mediates homologous recombination and cross-over between the human Ig gene segment on the recombination vector and the non-human mammal Ig gene segment on the BAC. Detection of homologously recombined BACs may utilize selectable and/or screenable markers incorporated into the vector. Humanized BACs can be readily isolated from the bacteria and used for producing knock-in non-human cells. Methods of recombining BACs and engineering insertions and deletions within DNA on BACs and methods for producing genetically modified mice therefrom are documented. See, e.g., U.S. Pat. No. 5,770,429; Fishwild, D. et al. (1996) *Nat. Biotechnol.* 14:845-851; Valenzuela et al. *Nature Biotech.* (2003) 21:652-659; Testa et al. *Nature Biotech.* (2003) 21:443-447; and Yang and Seed. *Nature Biotech.* (2003) 21:447-451.

The first recombination step may be carried out in a strain of *E. coli* that is deficient for sbcB, sbcC, recB, recC or recD activity and has a temperature sensitive mutation in recA. After the recombination step, a recombined DNA construct is isolated, the construct having the various sequences and orientations as described.

The regions used for BAC recombineering should be a length that allows for homologous recombination. For example, the flanking regions may be from about 0.1 to 19 kb, and typically from about 1 kb to 15 kb, or about 2 kb to 10 kb.

The process for recombining BACs to make larger and/or tailored BACs comprising portions of the Ig loci requires that a bacterial cell, such as *E. coli*, be transformed with a BAC carrying a first Ig locus, a portion thereof, or some other target sequence. The BAC containing *E. coli* is then transformed with a recombination vector (e.g., plasmid or BAC) comprising the desired Ig gene segment to be introduced into the target DNA, e.g., one or more human VH, DH and/or JH gene segments to be joined to a region from the mouse IgH locus, both of which vectors have a region of sequence identity. This shared region of identity in the presence of functional recA in the *E. coli* mediates cross-over between the Ig gene segment on the recombination vector and the non-human mammal Ig gene segment on the BAC. Selection and resolution of homologously recombined BACs may utilize selectable and/or screenable markers incorporated into the vectors. Humanized and chimeric BACs can be readily purified from the *E. coli* and used for producing transgenic and knock-in non-human cells and animals by introducing the DNA by various methods known in the art and selecting and/or screening for either random or targeted integration events.

Alternatively, the DNA fragments containing an Ig locus to be incorporated into a non-human animal are derived from DNA synthesized in vitro. The genomes of many organisms have been completely sequenced (e.g., human, chimpanzee, rhesus monkey, mouse, rat, dog, cat, chicken, guinea pig, rabbit, horse, cow, alpaca) and are publicly available with annotation. For many other organisms, there is publicly available information on the sequences of the transcriptome. In particular but not limited to, the human and mouse immunoglobulin loci have been studied and characterized for the location and activity of coding gene segments and non-coding regulatory elements.

The term "in silico," as used herein, refers to the use of a computer or computer algorithm to model a naturally occurring or in vitro process, and in particular, to assist in the design of a nucleotide or polypeptide sequence and/or the synthetic production of a nucleotide or polypeptide sequence using, all or in part, a cell free system (e.g., using automated chemical synthesis). The sequences of the Ig loci may be manipulated and recombined in silico using commonly available software for nucleic acid sequence analysis. In silico recombination may be within the same locus, between two loci from the same species, or between loci from two or more species. In silico recombination may be performed to design either a functional sequence or a non-functional, inactivated sequence. Precise nucleotide-by-nucleotide engineering allows for precise manipulation of sequence composition that can be applied to precisely engineer the function of the transgene and after transcription and translation, result in precisely engineered composition and function of the polypeptide product of the locus.

Sequences of an Ig locus may also be recombined in silico with those from a non-immunoglobulin locus, either from the same or a different species. Such sequences include, but are not limited to, genes for positive and negative drug selection markers such as G418, hyg, puro and tk, site-specific recombinase recognition sequences such lox P sites and its variants and frt sites, and precisely demarcated sequences for driving homologous recombination. After assembling the desired sequence in silico, it may then be synthesized and assembled without errors (Kodumal et al., *Proc. Natl. Acad. Sci.* (2004) 101:15573-15578). The synthesis, assembly and sequencing of large DNAs are provided on a contractual basis (e.g., DNA 2.0, Menlo Park, Calif.; Blue Heron Biotechnology, Bothell, Wash.; and Eurogentec, San Diego, Calif.). Such synthetic DNA sequences are carried in vectors such as plasmids and BACs and can be transferred into other vectors such as YACs.

The term "construct" as used herein refers to a sequence of DNA artificially constructed by genetic engineering, recombineering or synthesis. Constructs include, for example, transgenes and vectors (e.g., BACs, P1s, lambda bacteriophage, cosmids, plasmids, YACs and MACs). In one embodiment, the DNA constructs are linearized prior to introduction into a cell. In another embodiment, the DNA constructs are not linearized prior to introduction into a cell.

As used herein, "loxP" and "CRE" refer to a site-specific recombination system derived from P1 bacteriophage. loxP sites are 34 nucleotides in length. When DNA is flanked on either side by a loxP site and exposed to CRE mediated recombination, the intervening DNA is deleted and the two loxP sites resolve to one. The use of the CRE/lox system, including variant-sequence lox sites and variants of CRE, for which genetic engineering in many species, including mice, is well documented.

A similar system, employing frt sites and flp recombinase from *S. cerevisiae* can be employed to similar effect. As used herein, any implementation of CRE/loxP to mediate deletional events in mammalian cells in culture can also be mediated by the flp/frt system.

As used herein the terms "immunize," "immunization," and "immunizing" refer to exposing the adaptive immune system of an animal to an antigen. The antigen can be introduced using various routes of administration, such as injection, inhalation, ingestion or DNA immunization. Upon a second exposure to the same antigen, the adaptive immune response, i.e. T cell and B cell responses, is enhanced.

"Antigen" refers to a peptide, lipid, amino acid, nucleic acid, saccharide, hapten or chemical entity that is recognized by the adaptive immune system. Examples of antigens include, but are not limited to, bacterial cell wall components, pollen, and rh factor. "Target antigen" refers to an antigen, peptide, lipid, saccharide, or amino acid, which is recognized by the adaptive immune system that is chosen to produce an immune response against, e.g., a specific infectious agent or endogenous or exogenous cell or product thereof. Target antigens include, but are not limited to, bacterial and viral components, tumor-specific antigens, cytokines, cell surface molecules, any and all antigens against which antibodies or other binding proteins have been made by in vivo or in vitro methods, etc.

The term "pharmaceutical" or "pharmaceutical drug," as used herein refers to any pharmacological, therapeutic or active biological agent that may be administered to a subject or patient. In certain embodiments the subject is an animal, and preferably a mammal, most preferably a human.

The term "pharmaceutically acceptable carrier" refers generally to any material that may accompany the pharmaceutical drug and which does not cause an adverse reaction with the subject's immune system.

The term "administering," as used herein, refers to any mode of transferring, delivering, introducing, or transporting a pharmaceutical drug or other agent, such as a target antigen, to a subject. Such modes include oral administration, topical contact, intravenous, intraperitoneal, intramuscular, intranasal, or subcutaneous administration.

Non-Human Mammals and Cells Encoding Chimeric Ig Heavy Chains

Non-human animals and cells of the present invention comprise one or more altered Ig loci (e.g., IgH, Igκ, and/or Igλ) comprising non-endogenous Ig gene segments that replace the endogenous gene segments. In certain embodiments, the altered loci directly replace the endogenous gene segments. In other embodiments, the altered loci functionally replace the endogenous gene segments.

The non-endogenous gene segments may be derived from any species, and may include syngeneic gene segments. The non-endogenous sequence may be derived from, for example, humans, mice, non-human primates, camelids, rodents, bovines, ovines, equines, dogs, cats, goats, sheep, dolphins, bats, rabbits, and marsupials. As described above, the non-human cell or animal may be any non-human animal. Accordingly, the transgenic cells and animals described herein may comprise DNA sequences derived from any combination of species, provided that the animal is a non-human mammal. By way of example, chimeric mouse cells and mice comprising human or camelid Ig polynucleotide sequences are envisioned. In addition, the transgenic cell or animal may comprise non-endogenous DNA from more than one species. For example, a transgenic mouse genome can comprise both human and camelid DNA sequences.

The transgenic cells and animals described herein comprise one or more non-endogenous V gene segments. In specific embodiments, the preferred non-human animal is a mammal. In certain embodiments, the cell or animal further comprises one or more non-endogenous J gene segments. In another embodiment, a cell or animal comprising a chimeric IgH chain optionally further comprises one or more non-endogenous D gene segments.

In one embodiment, the cell or animal comprises a genome encoding a chimeric IgH chain and a transgenic light chain. The transgenic light chain may be an Igκ or an Igλ light chain. In addition, the transgenic light chain may be chimeric, or the transgenic light chain may comprise only non-endogenous amino acid sequences. In particular embodiments, the cell or animal comprises a genome encoding non-endogenous IgH, Igκ and Igλ gene segments. The transgenic cells and mammals comprising a chimeric IgH chain described herein comprise a non-endogenous CH1 domain that replaces a CH1 domain in a specific endogenous CH gene, e.g., Cμ, Cδ, or Cγ. In certain embodiments, the non-endogenous CH1 domain is orthologous to the endogenous CH region. In other embodiments, the non-endogenous CH1-domain is not orthologous to the endogenous CH region. In another embodiment, more than one endogenous CH1 domain is replaced with a non-endogenous CH1 domain. In a related embodiment, all of the endogenous CH1 domains are replaced with a non-endogenous CH1 domain. For example, an orthologous human CH1 may replace each of the endogenous Cγ genes (e.g., human Cγ1 CH1 replaces mouse Cγ1 CH1 and human Cγ2 CH1 replaces mouse Cγ2 CH1 etc.). In another embodiment, the CH1 domain that replaces the CH1 domain of each of the endogenous Cγ genes is a single human IgG isotype more frequently used in therapeutic mAbs, typically Cγ1, Cγ2 or Cγ4, so as to better facilitate in vivo maturation of a human V domain in the context of a more clinically relevant human CH1 domain.

Optionally, the upper hinge sequences of the endogenous C genes may also be replaced with orthologous non-endogenous C hinge sequences. Alternatively, the upper and middle hinge sequences of the endogenous C genes may also be replaced with the orthologous non-endogenous C hinge sequences, respectively. If human middle hinge regions are used, the human Cγ4 middle hinge sequence may be engineered to contain a proline at residue at position 229 rather than a serine in order to drive inter-heavy chain dimerization via disulfide bonds. The lower hinge region, a part of the CH2 domain, of the endogenous Cγ gene is not replaced in order to facilitate optimal binding to an endogenous FcγR. These three optional engineering strategies provide a non-endogenous heavy chain Fab domain, Fab domain plus upper hinge, or F(ab')$_2$, respectively. If the upper are replaced with human upper hinge regions, the variable region of the resulting antibody is more likely to retain optimal characteristics upon conversion to fully human IgG.

Another embodiment incorporates fully non-endogenous, e.g., human, Ig including the C regions comprising CH1-hinge-CH2-CH3(-CH4) and the cognate syngeneic, e.g., mouse, membrane and intracellular domains so as to provide native intracellular signal transduction and to enable association of the IgH in the B-cell receptor with Igα and Igβ and therein allow endogenous-type signaling from the Igα, Igβ and IgG containing B-cell receptor. In yet another embodiment, the membrane and intracellular domain of the heavy chain constant region are from the same or non-cognate syngeneic heavy chain isotypes. Such engineering of the constant region genes can be readily accomplished using methods of the invention as detailed below.

In yet another embodiment, the transgenic cells and animals comprising a chimeric IgH chain described herein comprise constant region encoded by a non-endogenous polynucleotide sequence derived from two or more species. For example, a transgenic mouse having a genome encoding a chimeric IgH chain constant region comprises a human CH1 domain, human upper hinge regions, and rat CH2 and CH3 domains, is envisioned. In animals having a xenogeneic constant region, it is preferred that the constant region is capable of interacting with (e.g., binding) an endogenous FcR.

In yet another embodiment, the transgenic cells and animals comprising a chimeric IgH chain described herein comprise constant region encoded by a non-endogenous polynucleotide sequence and endogenous polynucleotide sequence derived from two strains. For example, a transgenic mouse having a genome encoding a chimeric IgH chain constant region comprises a human CH1 domain, human upper hinge regions, and Balb/c mouse CH2 and CH3 coding sequences embedded into C57BL/6 ("B6") genomic DNA, comprising all B6 genetic information except that Balb/c-sequence exons for CH2 and CH3 replace their B6 counterparts, is envisioned.

In one embodiment, the composite IgH sequence comprises at least 3 kb upstream of the VH6 promoter through the D gene cluster through 3' of JH6 and is all human and in germline configuration. In another embodiment, the composite IgH sequence comprises at least 3 kb upstream of the VH6 promoter through the D gene cluster through 3' of JH6 and is all human and in germline configuration except that the D gene cluster is replaced by all or part of that of a xenogeneic species. In another aspect of the invention, there are additional human VH genes upstream of human VH6. In yet another aspect, the additional VH genes are in germline configuration. In an alternative aspect, the additional VH genes are sizes less than that in the human genome, unit sizes that comprise upstream regulatory elements such as cis-regulatory elements and binding sites for trans-acting factors, coding sequences, introns and 500 bp downstream of the last codon of each VH. In one aspect, the unit size is 10 kb or less. In another aspect, the unit size is 5 kb or less. In another aspect, the VH genes are selected from the subset of commonly shared VH genes amongst human haplotypes. In another aspect, VH genes, DH genes and JH genes are chosen to reflect a specific allele such as the most prevalent allele in human populations. In yet another aspect, the individual codons of the VH gene are codon-optimized for efficient expression in a specific non-human mammal. In another aspect the individual codons are optimized to be a template for somatic hypermutation.

In another embodiment, the composite IgH sequence comprises mouse DNA sequence starting at least 3 kb upstream of the promoter for the functional VH gene nearest the D gene cluster, e.g., VH5-2, through 3' of JH4 in germline configuration and into which the coding sequences have been replaced, all or in part, by human coding sequences, e.g., coding sequence for mouse VH5-2 is replaced by coding sequence for human VH6-1, mouse DH coding sequences replaced by human DH coding sequences and mouse JH coding sequences replaced by human JH coding sequences. In instances in which the number of human coding elements exceeds those in the mouse, e.g., 6 human JH coding sequences versus 4 mouse JH coding sequences, the additional JH genes may be included by various means, e.g., inserting the additional human JH coding sequences with their cis regulatory elements, such as recombination signal sequences downstream of the JH4, or omitted altogether.

In other embodiments, the mouse VH coding sequences are replaced, all or in part, by human VL coding sequences. In some embodiments, the entire DH gene cluster is of mouse sequence. In other embodiments, the entire DH gene cluster is of xenogeneic species. In another aspect of the invention, there are additional VH genes upstream of VH6 coding sequences, such that the all of the sequence is mouse except that coding sequences of functional VH genes are replaced with that of human VH genes.

In yet another aspect, the additional VH genes are in germline configuration. In an alternative aspect, the additional VH genes are sizes less than that in the mouse genome, unit sizes that comprise upstream regulatory elements such as cis-regulatory elements and binding sites for trans-acting factors, coding sequences, introns and 500 bp downstream of the last codon of each VH. In one aspect, the unit size is 10 kb or less. In another aspect, the unit size is 5 kb or less.

In another aspect, the VH genes are selected from a subset known to be functional, with the replacing human VH gene coding sequence being from a known functional human VH gene and replacing the mouse VH gene coding sequence of a known functional mouse VH gene. In another aspect, the human VH coding sequences are selected from the subset of commonly shared VH genes amongst human haplotypes. In another aspect, the replacing VH coding sequences, DH coding sequences and JH coding sequences are chosen to reflect a specific allele such as the most prevalent allele in human populations. In another aspect, some or all of the replacing VH coding sequences, DH coding sequences and JH coding sequences are from a xenogeneic species other than human. In yet another aspect, the individual codons of the VH gene are codon-optimized for efficient expression in a specific non-human mammal. In another aspect the individual codons are optimized to be a template for somatic hypermutation.

In another embodiment, the composite IgH sequence further comprises 3' of the most 3' JH the mouse sequence immediately downstream of mouse JH4 through Eμ through Cμ through Cδ through immediately 5' of the mouse Cγ3 promoter all in germline configuration with the exception of the replacement of the CH1 domains of mouse Cμ and Cδ by their human counterparts. In some instances, the mouse upper hinge regions are replaced by their respective human upper hinge regions. In a further embodiment, the mouse Cγ genes are configured in germline configuration with the exception of the replacement of their CH1 domains by human CH1 domains.

In some instances, the mouse upper hinge regions are replaced by human upper hinge regions. In some embodiments, the mouse Cγ3 coding sequences are replaced by human CH1 and mouse CH2, CH3, membrane and intracellular domains from Cγ1. In another embodiment, the complete germline-configured mouse Cγ3 sequence from the promoter upstream of the switch region through the intracellular domains and 3' untranslated sequence and poly (A) site are replaced by the complete corresponding sequences from Cγ1 in germline configuration with human CH1 replacing mouse CH1 from Cγ1 to effectively replace the complete Cγ3 gene by chimeric Cγ1. In some embodiments, a mouse constant coding sequence is replaced by human CH1 and mouse CH2, CH3, membrane and intracellular domains from different mouse constant region isotypes, e.g., CH2, CH3 and membrane domains from mouse Cγ2a and intracellular domain from Cμ. In still other embodiments the sequence of the CH2 and CH3 domains are furthered modified to modulate binding to Fc receptors, such as diminished binding to the inhibitory receptor, FcγR2b, therein producing a stronger secondary immune response.

In another embodiment, the cell or non-human animal comprises a locus encoding a human Ig light chain comprising a human Igκ variable region. In a related embodiment, the Ig light chain locus further comprises a human Igκ constant region. In one embodiment, the composite Igκ sequence comprises mouse DNA sequence from at least 3 kb upstream of the promoter of the Vκ gene most proximal to mouse Jκ1 (Vκ3-1) through 3' of mouse Jκ5 and is in germline configuration and into which the coding sequences have been replaced, all or in part, by human coding sequences, e.g., coding sequence for mouse Vκ3-1 is replaced by coding sequence for human Vκ4-1 and mouse Jκ coding sequences replaced by human Jκ coding sequences. In another embodiment the sequence from Jκ5 through Cκ is mouse and in germline configuration and into which the Cκ coding sequences have been replaced, all or in part, by human coding sequences.

In another aspect there is a 3'LCR region and RS element downstream of the Cκ gene. In one aspect, the 3' LCR and RS elements are mouse and in germline configuration. In another aspect of the invention, there are additional Vκ genes upstream of the coding sequences for human Vκ4-1, such that all of the sequence is mouse except that coding sequences of functional Vκ genes are replaced with that of human Vκ genes.

In yet another aspect, the additional Vκ genes are in germline configuration. In an alternative aspect, the additional Vκ genes are sizes less than that in the mouse genome, unit sizes that comprise upstream regulatory elements such as cis-regulatory elements and binding sites for trans-acting factors, coding sequences, introns and 500 bp downstream of the last codon of each Vκ. In one aspect, the unit size is 10 kb or less. In another aspect, the unit size is 5 kb or less. In another aspect, the Vκ genes are selected from the subset of commonly shared Vκ genes amongst human haplotypes. In another aspect, Vκ genes and Jκ genes are chosen to reflect a specific allele such as the most prevalent allele in human populations. In yet another aspect, the individual codons of the Vκ gene are codon-optimized for efficient expression in a specific non-human mammal. In another aspect the individual codons are optimized to be a template for somatic hypermutation.

In yet another embodiment, the human Ig light chain locus comprises all or a portion of a human Igλ light chain locus and an Igλ 3'LCR, or a functional fragment thereof. In one embodiment, the human Igλ light chain locus comprises the entire human Igλ locus. In another embodiment the human Igλ light chain locus comprises human Vλ coding sequences and 1 to 7 Jλ-Cλ coding sequence pairs, wherein the human Cλ is replaced with syngeneic Cλ. In yet another embodiment, the human Igλ light chain locus comprises human Vλ coding sequences, 1 to 7 human Jλ coding sequences, and a single human Cλ coding sequence, wherein the human coding sequences resemble a human Igλ locus configuration.

In particular embodiments, the Igλ 3' LCR, or a functional fragment thereof, is from a mammal selected from the group consisting of human, non-human primate, and rat. In one embodiment the Igλ 3' LCR, or a functional fragment thereof, is human. In particular embodiments, the Igλ 3' LCR, or a functional fragment thereof, binds NFκb. In one embodiment, the Igλ 3' LCR, or a functional fragment thereof, is from mouse and has been mutagenized so as to restore binding of NFκb. In other embodiments, the 3' LCR, or a functional fragment thereof, in the human Igλ locus is an Igκ 3' LCR, or functional fragment thereof.

In one embodiment, the composite Igλ sequence comprises at least 3 kb upstream of the Vλ 3r promoter through 3' of Jλ7-Cλ7 and is all human and in germline configuration. In another aspect, the sequence from Jλ7-Cλ7 through the λ 3' LCR is human and in germline configuration. In another aspect of the invention, there are additional human Vλ genes upstream of human Vλ 3r. In yet another aspect, the additional Vλ genes are in germline configuration. In an alternative aspect, the additional Vλ genes are sizes less than that in the human genome, unit sizes that comprise upstream regulatory elements such as cis-regulatory elements and binding sites for trans-acting factors, coding sequences, introns and 500 bp downstream of the last codon of each Vλ. In one aspect, the unit size is 10 kb or less. In another aspect, the unit size is 5 kb or less. In another aspect, the Vλ genes are selected from the subset of commonly shared Vλ genes amongst human haplotypes. In another aspect, Vλ genes and Jλ genes are chosen to reflect a specific allele such as the most prevalent allele in human populations. In yet another aspect, the individual codons of the Vλ gene are codon-optimized for efficient expression in a specific non-human mammal. In another aspect the individual codons are optimized to be a template for somatic hypermutation.

Production of Chimeric Cells and Animals

Specific embodiments of the invention provide methods of producing the animals and cells. In antibody producing mammals, for example, the endogenous Ig V, (D) and J genes are replaced by non-endogenous (e.g., human) Ig gene segments. In certain embodiments, the endogenous immunoglobulin (Ig) V, (D) and J genes are directly replaced by non-endogenous orthologs. In other embodiments, the endogenous genes are functionally replaced by non-endogenous orthologs while the endogenous genes are inactivated using various techniques as described herein and known in the art.

For example, one or more constructs carrying large portions of the non-endogenous V, D and J genes can replace all or a portion of the endogenous V, D and J genes. In certain embodiments, this can be done by homologously recombining the constructs into or adjacent to each Ig locus. Accordingly, the constructs can replace the endogenous sequences by sequential ("walking") replacement or by introducing two constructs into or adjacent to the endogenous Ig locus and subsequently removing intervening sequences.

An exemplary method of producing a cell having a genome that comprises a chimeric immunoglobulin heavy chain, wherein the heavy chain comprises a non-endogenous variable domain and a chimeric constant region, comprises the steps of (1) producing a first DNA construct, wherein the first construct comprises one or more non-endogenous VH, DH and/or JH gene segments, a first and a second flanking region, wherein the first flanking region is homologous to a DNA sequence 5' of the endogenous immunoglobulin heavy chain locus, and a first site specific recombination recognition sequence near the 3' end of the first construct; (2) producing a second DNA construct, wherein the second construct comprises one or more non-endogenous constant region gene segments, a third and a fourth flanking region, wherein the fourth flanking region is homologous to a DNA sequence 3' of the endogenous immunoglobulin heavy chain locus, and a second site specific recombination recognition sequence near the 5' end of the second construct; (3) homologously recombining the first and second constructs into the genome of a cell; and (4) introducing a site-specific recombinase into the cell, thereby removing an intervening sequence between the first and second site-specific recombinase recognition sequences.

Alternatively, the constructs can be introduced into non-human animal cells by transfection into cells in tissue culture or by pro-nuclear microinjection into fertilized eggs, and the non-endogenous sequences are randomly integrated into the genome. A separate functional inactivation (i.e., "knock-out") of the endogenous locus can be performed by gene targeting in mammalian cells in culture using the methods known in the art or described herein or by other methods such as the use of engineered zinc-finger nucleases or meganucleases.

A construct carrying all or part of the IgH locus downstream of JH can be engineered so that in each constant region gene, the endogenous CH1 domain is replaced with a non-endogenous CH1 domain. This can be accomplished by techniques known in the art, such as recombination of BACs in $E.\ coli$ or YACs in $S.\ cerevisiae$. Such replacement can also be accomplished using sequential homologous recombination driven knock-in replacement of the endogenous CH1 domain by the non-endogenous CH1 domain. Selectable markers used for the selecting recombinants can be flanked by site-specific recombinase recognition sequences, e.g. loxP sites and deleted via subsequent exposure to the site-specific recombines, e.g. CRE. Using different variant loxP sites to flank the selectable marker at each step restricts the CRE-mediated deletion to only the sequence between the specific loxP site and prevents longer-range deletion to an already existing loxP site. Alternatively, a construct carrying all or part of the IgH locus downstream of JH can be engineered so that in each constant region gene, the endogenous CH1 domain is replaced with a non-endogenous CH1 domain, using the ability to precisely synthesize and assemble DNAs based on published genome sequences of organisms such as humans and mice. Such synthesis and assembly is known in the art and is practiced by commercial entities (e.g., DNA2.0, Menlo Park, Calif.; Blue Heron Biotechnology, Bothell, Wash.).

According to one method of producing a cell comprising a chimeric heavy chain as described herein, a construct comprising the endogenous IgH loci downstream of the J gene cluster, wherein each retained C gene comprises a non-endogenous CH1-endogenous CH2-CH3 (and CH4 for Cλ), and membrane and intracellular domain exons is generated and introduced into the genome of a non-human cell. In certain embodiments, the construct is homologously recombined into or adjacent to the endogenous IgH locus. In other embodiments, the construct is randomly integrated into the genome of the cell. The construct may further comprise one or more non-endogenous V gene segments. In an alternative embodiment, the construct comprising the constant region gene segments is introduced into the genome of the cell either as a first introduction step to be followed by replacement of the endogenous V-D-J genes with non-endogenous V gene segments or in the opposite order, i.e., introduction of non-endogenous V gene segments followed by the introduction of the construct comprising the constant region gene segments engineered as described herein.

When using more than one construct to introduce non-endogenous Ig gene segments, the content of the Ig locus is not restricted to only constant region gene segments on one construct and variable region gene segments on the other. For example, a construct comprising C gene segments may also comprise one or more J gene segments, D gene segments and/or V gene segments. Similarly, a construct comprising V gene segments may further comprise one or more of D gene segments, J gene segments and/or C gene segments.

Constructs carrying the constant region genes may be engineered in vitro, in $E.\ coli$ or $S.\ cerevisiae$ or synthesized in vitro prior to introduction into ES cells so as to delete any unwanted or unneeded gene segments, such as the Cε and Cα genes. This would constrain the animals to making Cμ and Cδ for primary immune responses and Cγ isotypes for secondary, affinity-matured immune responses, from which therapeutic antibody candidates would typically be recovered.

In addition, constructs include both coding and non-coding polynucleotide sequences of which the non-coding polynucleotide sequences may be either non-endogenous or syngeneic polynucleotide sequences. For example, the endogenous (i.e., syngeneic) IgH 3' locus control region (LCR), or a portion thereof, are included downstream of the most 3' CH gene, Eμ, or a portion thereof is included between the most 3' JH and Cμ, and all or a portion of the Sμ and Sγ regions, promoters upstream of gene segments such as V gene segments and CH switch regions and recombination signal sequences (RSS). In addition, it is advantageous to include other intergenic regions that have been hypothesized to have gene regulation function such as the intergenic region between the most 3' VH gene the start of the D cluster and the intergenic region between Cδ and the first Cg switch region. Corresponding elements exist in the Ig light chain loci with documented function and location, e.g., Eκ, Igκ 3' LCR and Eδ. Because the endogenous mouse Igλ light chain locus possesses defective 3' LCRs, it is advantageous to use an orthologous functional Igλ 3' LCR from another species, e.g., human, rodent other than mouse, or to mutate the mouse 3' LCR to restore NFκb binding.

Similar strategies are employed for the endogenous Igκ locus except that a complete non-endogenous Cκ gene can be incorporated in the construct, thus producing fully non-endogenous Igκ chains. A non-endogenous Cλ locus could also be incorporated in a similar manner. For example, a construct comprising human Vκ and Cκ gene segments can be generated that encodes a fully human Igκ chain. Similarly, a construct comprising human Vλ and Cλ gene segments can be generated that encodes a fully human Igλ chain.

Yet another aspect of the invention comprises incorporating fully human Ig loci, including human C regions, in place of the complete endogenous Ig loci. In an additional embodiment, a cluster of endogenous FcR genes is also replaced with an orthologous cluster of human FcR genes using similar BAC-based genetic engineering in homologous recombination competent cells, such as mouse ES cells. The cluster of endogenous FcγR genes can be directly replaced in the same ES cell in which the human IgH locus or portions thereof have replaced the endogenous locus or in a separate ES cell. Alternatively, the cluster of endogenous FcγR genes can be functionally replaced in the same ES cell in which the human IgH locus or portions thereof have replaced the endogenous locus or in a separate ES cell. In the latter instance, mice would be derived from said ES cells and bred with mice carrying the engineered Ig locus (loci) so as to produce mice that make human IgG antibodies that bind to human FcγR in place of mouse FcγR genes. In either way fully human antibodies would be produced and during an immune response would be able to engage the human FcR receptors normally. Such transgenic animals would also have the benefit of being useful for testing for the activity and effector function of human therapeutic mAb candidates in models of disease when bred onto the appropriate genetic background for the model, i.e., SCID, nu/nu, nod, and lpr mice. Further, the human target gene sequence can replace the endogenous gene using BAC targeting technology in homologous recombination-competent cells, providing models for target validation and functional testing of the antibody. In this instance, the human CH genes may be engineered to have cytoplasmic and/or membrane domain gene segments from mouse or other orthologous species to facilitate native signal transduction in the B cell. Alternatively to replacing the entire endogenous FcγR locus with the complete complement of wild-type genes in the human FcγR locus, certain FcγR could be mutated to have attenuated function or deleted entirely. For example, mutation to render the inhibitory human FcγR2b inactive and having simultaneous inactivation of the mouse orthologue would render the genetically engineered mouse carrying both mutations more susceptible to developing autoreactive B cells, with a consequent potential benefit of broadening the fully human antibody response against antigens.

In addition, another aspect of the invention relates to the design of the desired non-endogenous V region (e.g., human). In particular, an entire V domain repertoire, or a portion thereof, may be incorporated into the genome of the cell, or a tailored V domain repertoire may be incorporated. For example, in certain embodiments it is preferred to omit V domain gene segments that are missing from some human haplotypes and instead tailoring the V domain repertoire to be composed of only the functional V gene segments common across all known human haplotypes. Doing so provides antibody drug candidates with V domains that are better immune tolerized across all potential patients, thereby preventing the induction of a dangerous immune response upon administration of the encoded antibody to a subject. One or more V domain gene segments may be incorporated into the genome of a cell.

In certain embodiments of the invention, constructs containing the desired Ig loci gene segments are used to incorporate the genetic information into the target cell genome via homologous recombination. In particular, the nature of BAC engineering in *E. coli* provides additional opportunities to finely tailor the immunoglobulin loci prior to introduction into competent cells. BAC libraries and the complete sequence of the Ig loci are available for many species. Synthetic constructs can also be finely tailored as described herein.

The ability to finely tailor the constructs described herein provides the ability to introduce specific non-endogenous and syngeneic components. For example, the non-endogenous DH cluster can be replaced or supplemented with D genes from other species, such as from non-human primate, rabbit, rat, camelid, hamster etc. D gene segments within the IgH loci can be defined from publicly available sequence or genetic structure information, or by testing using appropriate D specific probes or primers. The orthologous D gene clusters or portions thereof can be homologously recombined into the constructs or assembled in silico and then synthesized, therein replacing or adding to the cluster of non-endogenous D gene segments.

Because of the significant diversification that occurs in making the complementarity determining region-3 (CDR3) and because the structure of the V region is such that the CDR3 is relatively solvent inaccessible, immunogenicity to the CDR3 sequence is of less concern. Therefore, amino acids encoded by non-human D genes incorporated into the CDR3 are less likely to be immunogenic upon administration to a human. D genes derived from another species could confer an advantage by producing novel CDR3 structures that would expand the range of epitope specificities and affinities in a panel of antigen-specific antibodies, therein broadening the quality of activities mediated by a panel of mAbs.

Similarly, the JH gene cluster, i.e., one or more JH gene segments, can be from a different non-endogenous species due to the relative sequence conservation across mammals. The JH gene segment may be derived from any animal, e.g., human, non-human primate, rabbit, sheep, rat, hamster, camelid and mouse. In particular embodiments, the JH gene segment is human.

In further aspects, after engineering the Ig loci constructs, they are introduced into non-human mammalian cells and are randomly integrated into the genome. Methods for introducing one or more constructs comprising the altered Ig locus, or portion thereof, include, for example, electroporation, lipofection, calcium phosphate precipitation, *E. coli* spheroplast fusion, yeast spheroplast fusion and microinjection, either into the pronucleus of a fertilized egg to make transgenic animals directly or into cells cultured in vitro. In certain embodiments, the construct is engineered to carry a selectable marker gene, e.g., $G418^R$, hygromycin$^R$, puromycin$^R$, 5' of the most 5' V gene. A selectable marker gene may also be 3' of the most 5' V gene. The selectable marker gene may be flanked by site-specific recombinase recognition sequences, which if brought into the presence of recombinase, will recombine and delete the intervening selectable marker. This is particularly important if a selectable marker cassette is located 3' of the most 5' V gene and near an enhancer sequence so as to not attenuate the function of the enhancer.

In certain embodiments, two or more constructs, such as BACs, are introduced into the cell in a single step. If two constructs are introduced into the cell simultaneously, they will typically co-integrate. Some of the co-integrated constructs will integrate in a functional head-to-tail fashion with, for example, V, (D) and J segments operably oriented 5' of C region gene segments. Co-introduced constructs can be any combination of BACs, YACs, plasmids, bacteriophage, P1s etc. In some instance, there will be a single-copy integration of the two constructs, creating a single-copy transgene. In other instances, there will be a multi-copy integration of the two constructs. Multi-copy integration is not necessarily undesirable as it can yield beneficial consequences, such as increased expression of the transgene, resulting in more of the desired gene product. However, if a single copy of the transgene is desired, there are in vitro and in vivo processes for doing so.

For instance, if a site-specific recombinase sequence is positioned at the 3' end of the 5' construct and if a site-specific recombinase sequence is positioned at the 5' end of the 3' construct, resulting co-integrants of the 5' construct and the 3' construct both oriented in the 5' to 3' manner will have site-specific recombinase sequences oriented so that any intervening sequence between the terminal 5' construct and the terminal 3' construct would be deleted upon exposure to the site-specific recombinase, and thus the terminal 5' construct becomes operably linked to the terminal 3' construct, resulting in a single copy transgene. This process may be conducted either in vitro in culture mammalian cells or in vivo in transgenic animals expressing the recombinase (for example of resolving a multi-copy single construct transgene into a single-copy transgene in vivo, see Janssens et al. *Proc. Natl. Acad. Sci.* (2006) 103: 15130-15135.) Functional transgenes can also be made by pronuclear co-microinjection of 3 or more constructs (see US Patent Application Publication No. 2010/0077497.)

After introducing the Ig locus or loci described herein into the genome of a cell to replace (e.g., functionally replace) an endogenous Ig locus, or portion thereof, a non-human animal can be produced. If the non-human mammalian cells are embryonic stem cells, genetically engineered non-human mammals, such as mice and rats, can be produced from the cells by methods such as blastocyst microinjection followed by breeding of chimeric animals, morula aggregation. If the cells are somatic cells, cloning methodologies, such as somatic cell nuclear transfer, can be used to produce a transgenic animal. Multi-stage breeding is used to produce animals heterozygous or hemizygous for modified IgH and IgL loci (either Igκ or Igλ, or both Igκ and Igλ). Mice with modified IgH and IgL loci can be further bred to produce mice homozygous for IgH and IgL (either Igκ or Igλ, or both Igκ and Igλ).

The engineered Ig loci described herein will function in the non-human animals. By using appropriate detection reagents, e.g., anti-human CH1 domain antibodies or anti-human CL antibodies, it is possible to detect the antibodies produced by the engineered locus even in the presence of antibodies expressed from an active endogenous locus. Furthermore, in a mouse, for example, it is possible to use allotypic sequences in the mouse portion of the constant region of the transgene that are different from the allotypic sequence of the constant region of the recipient mouse strain, e.g., mouse IgH a allotypes (Balb/c) versus IgH b allotypes (C57BL/6).

Inactivation of Endogenous Ig Loci

In certain embodiments, it may be desirable to functionally inactivate one or more of the endogenous Ig loci in the recipient non-human mammal. Various methods known in the art can be used to inactivate the endogenous Ig loci. An animal comprising an engineered Ig transgene is bred with an animal comprising one or more inactivated endogenous loci to derive an animal capable of expressing antibodies from the Ig transgene and without production of the complete native immunoglobulin from the inactivated endogenous loci with the Ig transgene therein functionally replacing the inactivated endogenous locus.

The very fine tailoring of DNA sequences by combining in silico recombination with in vitro DNA synthesis and assembly technologies allows for the precise deletion and/or modification of the homologous target sequences. For instance, recombination signal sequences or splice donor sequences for specific gene segments, e.g., J gene, may be altered or deleted.

Components of an IgH locus that may be altered to down modulate and/or abrogate locus function include the JH cluster (complete deletion, removal of recombination signal sequences (RSS), splice donor sequences or all or some of the above) (see, for example, U.S. Pat. No. 5,939,598), Eμ, Cμ and Cδ, the D gene cluster (complete deletion, removal of recombination signal sequences (RSS), splice donor sequences or all or some of the above), the VH genes (complete deletion, removal of recombination signal sequences (RSS), splice donor sequences or all or some of the above), and all of the constant region genes. Placing a strong constitutive promoter such as PGK in the position of critical enhancer elements such as Eμ can have severe deleterious consequences on locus function, effectively bringing about inactivation.

Components of an Igκ locus that may be altered to down modulate and/or abrogate locus function include the Jκ cluster (complete deletion, removal of recombination signal sequences (RSS), splice donor sequences or all or some of the above), Eκ, Cκ, and the Vκ genes (complete deletion, removal of recombination signal sequences (RSS), splice donor sequences or all or some of the above).

Components of the Igλ locus that may be altered to down modulate and/or abrogate locus function include the Jλ cluster (complete deletion, removal of recombination signal sequences (RSS), splice donor sequences or all or some of the above), Eλ, Cλ, and the Vλ genes (complete deletion, removal of recombination signal sequences (RSS), splice donor sequences or all or some of the above). Deletion of larger sequence units such as the entire Igλ locus, the entire VH gene repertoire of the IgH locus etc. may be effected by serial insertion of site-specific recombination sequences (lox P or frt) adjacent to the 5' and 3' ends of the sequence to be deleted followed by transient expression of the relevant recombinase, e.g., CRE or FLP. Various methods known in the art can be used to inactivate the endogenous Ig loci. See for example: Chen J., et al. *Int Immunol.* 1993 June; 5(6): 647-56; Jakobovits et al., *Proc. Natl. Acad. Sci.* (1993) 90: 2551-2555; Nitschke et al. *Proc. Natl. Acad. Sci.* (1993) 90: 1887-1891; U.S. Pat. No. 5,591,669; Afshar et al., *J. Immunol.* (2006) 176: 2439-2447; Perlot et al. *Proc. Natl. Acad. Sci.* (2005) 97: 14362-14367; Roes and Rajewsky *J. Exp Med.* (1993) 177: 45-55; Lutz et al. *Nature* (1998) 393: 797-801; Ren et al. *Genomics* (2004) 84: 686-695; Zou et al. *EMBO J.* (1993) 12: 811-820; Takeda et al. *EMBO J.* (1993) 12: 2329-2336; Chen et al. *EMBO J.* (1993) 12: 821-830; Zou et al., *J. Immunol.* (2003) 170: 1354-1361; Zheng et al. *Molec. Cell. Biol.* (2000) 20: 648-655; Zhu et al. *Proc. Natl. Acad. Sci.* (2000) 97: 1137-1142; Puech et al. *Proc. Natl. Acad. Sci.* (2000) 97: 10090-10095; LePage et al. *Proc. Natl. Acad. Sci.* (2000) 97: 10471-10476; Li et al. *Proc. Natl. Acad. Sci.* (1996) 93: 6158-6162.

In some embodiments, multiple deletions or multiple mutations are introduced into an endogenous Ig locus to inactivate the endogenous immunoglobulin locus, thereby solving the problem of partially inactivating an endogenous Ig locus. In particular, the two or more mutations independently impair both the formation of a functional variable domain and the formation of a constant region capable of driving primary B cell development. The mutations impair primary B cell development because the resulting Ig sequence prevent formation of an IgH capable of mediating signal transduction (by itself or in association with Igα and/or Igβ), e.g., gene rearrangement is blocked, transcription or translation of a complete product fails, or the product cannot signal.) In one instance, the endogenous J genes, Eμ, Cμ and Cδ are deleted. In another instance, the endogenous J genes, Eμ, Cμ and Cδ are all replaced with a single drug-resistance cassette that is transcriptionally active in ES cells and B cells. An example of a drug-resistance cassette for use in mice is the PGK-G418 neomycin resistance cassette comprising the mouse pgk-1 promoter. Taken together, this deletion blocks V-D-J recombination (J deletion and Eμ replacement by an active expression cassette) and primary B cell receptor signaling (deletion of Cμ and Cδ) and anchoring in the B cell membrane. The inactivation of multiple components produces multiple layers of redundancy for inactivating the IgH locus at different developmental stages, creating a failsafe against any one residual activity rescuing B cell development.

Other combinations of deletions or mutations can also be performed. For example, the entire C gene cluster may be deleted in combination with a JH deletion. Deletion of the entire D gene cluster in combination with Cµ and Cδ would also be effective. Any combination of one or more mutations are contemplated herein as long as the resulting mutations impair formation of a functional variable region and formation of a membrane-anchored heavy chain constant region capable of signal transduction, either directly or in combination with the accessory signal transducing proteins Igα and/or Igβ.

Not all of each module needs to be deleted. For instance, a portion of J, Cµ or Cδ genes may be left in the immunoglobulin locus so long as one or more cis regulatory elements such as recombination signal sequences (RSS), splice donor, and splice acceptor sequences are deleted or mutated or the formation of a functional open reading frame is obviated. Current methodologies for mutating or synthesizing precise DNA sequences enable the creation of very specific, even single nucleotide, mutations to be introduced. This provides the benefit of allowing for optimal positioning of the DNA arms driving homologous recombination in ES cells while still inactivating the locus.

Deletion of portions of the IgH locus can be made in cells using homologous recombination techniques that are now standard for genetic engineering. Deletions may be made in one step or in multiple steps, and they may be generated using one or more constructs. The deletions could also be made using site-specific recombinase systems such as Cre-lox or Flp-Frt. A combination of homologous recombination and site-specific recombinase systems may be used. Other systems such as engineered zinc-finger nucleases injected into fertilized eggs may be used to engineer deletions into the genes, in one or more steps to build up the number of deleted or mutated modules of the IgH locus.

A similar strategy may be employed for inactivating the endogenous immunoglobulin kappa light chain and/or lambda light chain. The important modules for inactivation are conserved, particularly the J, E (intronic enhancer) and C regions, between all of the Ig loci. In embodiments regarding the inactivation of an Ig light chain locus, inactivation of the constant region will prevent the formation of a complete antibody molecule or a Fab domain in that the light chain constant region is unable to form a disulfide bond with the heavy chain.

For example, an endogenous Igκ locus can be inactivated by replacing the J genes, Eκ, and Cκ with a single drug-resistance cassette that is transcriptionally active in ES cells and B cells, such as the PGK-G418 neomycin resistance cassette. Taken together, this deletion blocks V-J recombination (J deletion and Eκ replacement by an active expression cassette) and pairing of an Igκ light chain with a heavy chain in an antibody (deletion of Cκ). Any combination of one or more mutations are contemplated herein as long as the resulting mutations impair formation of a functional variable region and formation of a light chain constant region capable of forming a disulfide bond with a heavy chain.

In another embodiment, all of the J-C pairs of the Igλ locus 3' of the Vλ gene segment can be deleted using a site-specific recombinase system, such as Cre/loxP. The deletion of all of the J segment genes prevents V-J rearrangement, and therefore impairs the formation of a functional variable region. The deletion of the Cλ gene segments prevents the formation of a functional constant region, thereby preventing the formation of a constant region capable of forming a disulfide bond with any IgH chain. In yet another embodiment, inactivation of the mouse Igλ is achieved through two separate inactivations. The first is inactivation is of Vλ1 and the second is inactivation is of both Vλ2 and Vλx. The second inactivation may be done before the first inactivation. Inactivation may be achieved through inactivation of RSS 5' or 3' of each of the Vλ genes, inactivation of the promoters 5' of each gene, or inactivation of the coding sequences. The inactivation may be through mutation, either point, insertion or deletion, to render non-functional, or complete deletion.

The endogenous Ig locus of a non-human cell may be inactivated by homologous recombination with one or more constructs designed to introduce the deletions or mutations capable of impairing both the formation of a functional variable domain and the formation of a constant region capable of driving primary B cell development. Methods for effecting homologous recombination in mouse and rat ES cells are known in the art. Upon homologous recombination between the flanking regions located on the construct and the corresponding homologous endogenous DNA sequences in the cell, the desired deletions or mutations are incorporated into the endogenous Ig locus.

Cells that have undergone a correct recombination event can be screened for using positive and negative selection markers, such as drug resistance. To further confirm homologous recombination, genomic DNA is recovered from isolated clones and restriction fragment length polymorphism (RFLP) analysis performed by a technique such as Southern blotting with a DNA probe from the endogenous loci, said probe mapping outside the replaced region. RFLP analysis shows allelic differences between the two alleles, the endogenous DNA and incoming DNA, when the homologous recombination occurs via introduction of a novel restriction site in the replacing DNA.

Various assays known in the art, including, but not limited to, ELISA and fluorescence microscopy, may be used to confirm that the mutations introduced into the endogenous Ig locus impair the expression of a functional Ig heavy or light chain by the cell. An absence of the endogenous Ig heavy or light chain indicates that its expression is impaired. Other well known assays, such as RT-PCR, can determine whether or not the modified locus is able to be transcribed.

Cells having one or more inactivated Ig loci may be used to produce transgenic non-human animals, e.g., mice, that have one or more inactivated Ig loci. After engineering the mutated Ig locus into non-human cells to delete or replace portions of the endogenous Ig loci, genetically engineered non-human mammals, such as mice, can be produced by now-standard methods such as blastocyst microinjection followed by breeding of chimeric animals, morula aggregation or cloning methodologies, such as somatic cell nuclear transfer.

Breeding Strategies

Certain embodiments provide a method of producing a non-human mammal having a genome encoding non-endogenous VH and CH1 gene segments and a non-endogenous Ig light chain locus comprising the steps of breeding a non-human mammal comprising a chimeric Ig heavy chain locus, wherein the Ig heavy chain locus comprises the non-endogenous VH and CH1 gene segments, with a non-human mammal comprising a non-endogenous Ig light chain locus; selecting offspring having a genome comprising the chimeric Ig heavy chain locus and the non-endogenous Ig light chain locus; further breeding the offspring; and producing offspring having a genome homozygous for the chimeric heavy and non-endogenous light chain loci. In related embodiments, the genome of the mammal also encodes a non-endogenous JH gene segment.

Further embodiments comprise selecting offspring having a genome comprising the chimeric Ig heavy chain locus and the non-endogenous Ig light chain locus; further breeding the offspring with non-human mammals having functionally inactivated endogenous Ig loci; and producing offspring and further breeding to produce offspring having a genome homozygous for functionally inactivated endogenous Ig loci, the chimeric heavy and the non-endogenous light chain loci. In related embodiments, the genome of the mammal also encodes a non-endogenous JH gene segment.

The genetic engineering strategies described herein can be applied to engineering of mice and other animals so as to express non-endogenous sequence V regions coupled with xenogeneic C regions, or completely non-endogenous antibodies, or some intermediate thereof. For animals for which there is a current lack of ES cell technology for genetic engineering through blastocyst microinjection or morula aggregation, the endogenous loci can be modified in cells amenable to various cloning technologies or developmental reprogramming (e.g., induced pluripotent stem cells, IPS). The increased frequency of homologous recombination provided by the BAC technology provides the ability to find doubly replaced loci in the cells, and cloned animals derived therefrom would be homozygous for the mutation, therein saving time and costs especially when breeding large animals with long generation times. Iterative replacements in the cultured cells could provide all the requisite engineering at multiple loci and then direct production of animals using cloning or IPS technology, without cross-breeding, to produce the appropriate genotype. The ability to finely tailor the introduced Ig genes and also finely specify the sites into which they are introduced provides the ability to engineer enhancements that provide better function. Engineered animals such as goats, bovines, ovines, equines, rabbits, llamas, dogs etc. are a source of fully human polyclonal antibodies.

Furthermore, if BACs are engineered in *E. coli* with DNA components required for chromosome function, e.g., telomeres and a centromere, preferably, but not required, of the recipient species for optimal function, e.g., mouse telomeres and a mouse centromere, they can be introduced into the recipient cell by electroporation, microinjection etc. and function as artificial chromosomes. These BAC-based artificial chromosomes also can be used as a foundation for subsequent rounds of homologous recombination for building up larger artificial chromosomes.

The engineered Ig locus or loci described herein provided on vectors such as plasmids, BACs or YACs can also be used as standard transgenes introduced via microinjection into the pronucleus of an embryo such as mouse, rabbit, rat, or hamster. Several BACs, YACs, plasmids or any combination thereof can be co-microinjected and will co-integrate to make a functional locus. Various methods known in the art and described herein can be used to inactivate the endogenous Ig loci and the animals with an engineered Ig transgene bred with those with one or more inactivated endogenous loci to derive genotypes expressing antibodies from the transgene and without production of the complete native immunoglobulin from the inactivated endogenous loci.

Antibodies

A chimeric antibody, or antigen-binding fragment thereof, as disclosed herein comprises a non-endogenous variable domain and a chimeric heavy chain constant region. In particular, the chimeric heavy chain constant region comprises a non-endogenous CH1 domain. In certain embodiments, the chimeric antibody comprises a chimeric heavy chain and a non-endogenous light chain. In other embodiments, the chimeric antibody comprises a chimeric heavy chain and an endogenous light chain. In one embodiment, the chimeric heavy chain variable region is encoded by polynucleotide sequences derived from two or more non-endogenous species.

In certain embodiments, the chimeric heavy chain comprises a non-endogenous upper hinge region. In a related embodiment, the chimeric heavy chain comprises non-endogenous upper and middle hinge regions.

Eukaryotic Transgenes Comprising Sequences Designed in silico and Made Synthetically The ability to obtain sequences, for genes, loci and full genomes, and transcriptome sequences, either from public databases with annotations, or derived using commercially available sequencing technology, or derived through commercial operation performing sequencing on a contractual basis, means that DNA sequences can be readily manipulated in silico, e.g., taken apart and reassembled, either within genes or loci, or between genes or loci, across the same species, different strains of a species, or across two or more different species. Heretofore eukaryotic transgenes, particularly metazoans, have been constructed from DNAs derived from a natural source. These natural source DNAs include genomic DNA libraries cloned into various vectors such plasmid, bacteriophage, P1s, cosmids, BACs, YACs and MACs and cDNA libraries cloned into vectors, generally plasmids or bacteriophage. Methodologies for recombining DNAs carried on these vectors and for introducing small alterations such as site-directed mutations are well known in the art and have been deployed to make transgenes composed of sequence that overall conforms to the sequence of the parental DNA in the library from which they were isolated. In some instances, portions of DNA are missing from the library, or a library from the desired animal, strain or haplotype thereof may be unavailable and not able to be constructed using ordinary skill in the art.

For example, there may be preferred allelic variants to be included in a transgene and said allelic variant is not available in any library and, furthermore, source nucleic acid such as RNA or DNA may not be available. In complex loci with many genes or exons and cis regulatory elements, it can be technically infeasible to procure and recombine into one transgenes the DNAs encoding such if they are from different species and strains or haplotypes. Thus, the means by which to create DNA of complexly engineered, particularly from a completely in silico design, is not possible using standard methodologies.

Synthetic means of creating DNA sequences have been described, are commercially available and can be used to make DNA sequences based on a completely in silico design. However, whether they can be introduced and, in particular, expressed in eukaryotes, particularly metazoans, has heretofore been unknown.

Some of the Ig transgene constructs disclosed herein comprise such complex sequence composition that they cannot be engineered to the desired precision and accuracy by previously described means. Further contemplated transgene structures include a germline configured DNA in which are replaced only coding sequences, all or a part thereof, by non-endogenous coding sequences so that all of the cis regulatory sequences are endogenous, retaining completely native gene regulation optimal for, position-independent, copy-number dependent, tissue-specific, developmental-specific gene regulation, e.g., an IgH sequence which comprises completely mouse DNA except for sequences encoding human VH, DH, JH, CH1 and upper hinge sequences replacing their mouse orthologues; an FcγR sequence which comprises completely mouse DNA except for sequences encoding human FcγR replacing their mouse orthologues; an IgH sequence which comprises completely mouse DNA except for sequences encoding camelid VH, DH, JH, sequences replacing their mouse orthologues; an IgH sequence which comprises completely mouse DNA except for sequences encoding human VH, JH, CH1 and upper hinge sequences replacing their mouse orthologues and non-human, non-mouse DH coding sequences, e.g., rabbit, replacing their mouse orthologues; an IgH sequence which comprises completely mouse DNA except for sequences encoding VH, DH, JH, from a species relevant to animal healthcare, e.g., canine, feline, ovine, bovine, porcine, replacing their mouse orthologues; an IgL sequence which comprises completely mouse DNA except for sequences encoding human VL, JL, and optionally CL, replacing their mouse orthologues; an IgL sequence which comprises completely mouse DNA except for sequences encoding camelid VL, JL, and optionally CL, replacing their mouse orthologues; an IgL sequence which comprises completely mouse DNA except for sequences encoding VL, JL, and optionally CL from a species relevant to animal healthcare, e.g., canine, feline, ovine, bovine, porcine, replacing their mouse orthologues. Other examples include deleting unneeded or undesirable DNA sequences, e.g., V genes that are pseudogenes, V genes that produce products that can misfold, V genes that are absent from some human haplotypes, large tracts of non-regulatory DNA, CH genes not therapeutically important. Other examples include altering DNA sequences for optimizing transgene function or producing a desired product therefrom, e.g., using the most prevalent allele of a V gene, repairing the mouse Igλ 3' enhancer to restore NFκb binding. Transgenes may comprise parts that are synthetic and parts that are from natural sources. DNAs for inactivating genes may also comprise synthetic DNA, all or in part. Moreover, the method for transgene construction described herein is not limited to immunoglobulin loci. Any transgene can be constructed by the steps of first using in silico methods to recombining and assemble the sequence from various DNA sequence and second of employing available synthetic DNA methods to create the physical DNA.

Methods of Producing Antibodies

An animal carrying the modified locus or loci can be immunized with an antigen using various techniques available in the art. Antigens may be selected for the treatment or prevention of a particular disease or disorder, such as various types of cancer, graft versus host disease, cardiovascular disease and associated disorders, neurological diseases and disorders, autoimmune and inflammatory disorders, and pathogenic infections. In other embodiments, target antigens may be selected to develop an antibody that would be useful as a diagnostic agent for the detection one of the above diseases or disorders.

Antigen-specific repertoires can be recovered from immunized animals by hybridoma technology, single-cell RT-PCR for selected B cells, by antibody display technologies, and other methods known in the art. For example, to recover human/mouse chimeric mAbs from mouse-derived hybridomas, a human V-CH1-mouse hinge+CH2+CH3 antibody or a human V-CH1-upper/middle hinge-mouse lower hinge+CH2+CH3 antibody (depending upon the IgH locus engineering) is secreted into the culture supernatant and can be purified by means known in the art such as column chromatography using protein A, protein G, etc. The purified antibody can be used for further testing and characterization of the antibody to determine potency in vitro and in vivo, affinity etc.

In addition, since they can be detected with an antibody specific for the endogenous constant region used as a secondary agents, a human V-CH1 (upper/middle hinge)-non-human CH2-CH3 mAb may be useful for immunochemistry assays of human tissues to assess tissue distribution and expression of the target antigen. This feature of the chimeric antibodies of the present invention allows for specificity confirmation of the chimeric mAb over fully human mAbs because of occasional challenges in using anti-human constant region secondary detection agents against tissues that contain normal human Ig and from the binding of human Fc regions to human FcR expressed on cells in some tissues.

The non-endogenous variable regions of the mAbs can be recovered and sequenced by standard methods. Either before or after identifying lead candidate mAbs, the genes, either genomic DNA or cDNAs, for the non-endogenous VH and VL domains can be recovered by various molecular biology methods, such as RT-PCR, and then appended to DNA encoding the remaining portion of the non-endogenous constant region, thereby producing a fully non-endogenous mAb. For example, a fully human mAb may be generated. The DNAs encoding the now fully non-endogenous VH-CH and non-endogenous VL-CL would be cloned into suitable expression vectors known in the art or that can be custom-built and transfected into mammalian cells, yeast cells such as Pichia, other fungi etc. to secrete antibody into the culture supernatant. Other methods of production such as ascites using hybridoma cells in mice, transgenic animals that secrete the antibody into milk or eggs, and transgenic plants that make antibody in the fruit, roots or leaves can also be used for expression. The fully non-endogenous recombinant antibody can be purified by various methods such as column chromatography using protein A, protein G etc.

A purified antibody can be lyophilized for storage or formulated into various solutions known in the art for solubility and stability and consistent with safe administration into animals, including humans. Purified recombinant antibody can be used for further characterization using in vitro assays for efficacy, affinity, specificity, etc., animal models for efficacy, toxicology and pharmacokinetics etc. Further, purified antibody can be administered to humans and non-human animals for clinical purposes such as therapies and diagnostics for disease.

Various fragments of the non-endogenous V-CH1-(upper/middle hinge)-endogenous CH2-CH3 mAbs can be isolated by methods including enzymatic cleavage, recombinant technologies, etc. for various purposes including reagents, diagnostics and therapeutics. The cDNA for the repertoire of non-endogenous variable domains+CH1 or just the non-endogenous variable domains can be isolated from the engineered non-human mammals described above, specifically from RNA from secondary lymphoid organs such as spleen and lymph nodes, and the VH and VL cDNAs implemented into various antibody display systems such as phage, ribosome, E. coli, yeast, mammalian etc. The transgenic mammals may be immunologically naïve or optimally may be immunized against an antigen of choice. By using appropriate PCR primers, such as 5' in the leader region or framework 1 of the variable domain and 3' in the human CH1 of Cγ genes, the somatically matured V regions can be recovered in order to display solely the affinity-matured repertoire. The displayed antibodies can be selected against the target antigen to efficiently recover high-affinity antigen-specific Fv or Fabs, and are void of the endogenous CH2-CH3 domains that would be present if mAbs were recovered directly from the mammals. Moreover, it is not necessary that the animals carrying the IgH and IgL transgene be functionally inactivated for the endogenous Ig loci. Animals heterozygous for IgH and IgL loci, or animals carrying the IgH and IgL transgenes and heterozygous for inactivated endogenous IgH and IgL loci, which produce the chimeric antibodies described herein as well as both fully-endogenous antibodies (e.g., mouse antibodies) and mixed endogenous and non-endogenous antibodies (e.g., human-mouse antibodies), can also be used to generate antigen-specific non-endogenous V endogenous C mAbs (e.g., human V-mouse C mAbs). Animals carrying just one Ig transgene, e.g., IgH, could be used as a source of non-endogenous (e.g., human) VH domains (VH-CH1) and other animals carrying just one different Ig transgene, e.g., IgL, either Igκ or Igλ, could be used as a source of non-endogenous (e.g., human) VL domains (VL-CL) and then the VH-CH1 and VL-CL sequences combined into an antibody display library to display fully human antibodies. In such animals, both, one or none of the endogenous Ig loci may be activated. The animals may be immunized so as to enable recovery of affinity-mature VH and VL. For example, an antibody display library from two separate mice—one with human VH-CH1-mouse CH2-CH3 and the other with human Vκ-Cκ—could be used to recover fully human antibodies using well-established techniques in molecular biology.

Methods of Use

Purified antibodies of the present invention may be administered to a subject for the treatment or prevention of a particular disease or disorder, such as various types of cancer, graft versus host disease, cardiovascular disease and associated disorders, neurological diseases and disorders, autoimmune and inflammatory disorders, allergies, and pathogenic infections. In preferred embodiments, the subject is human.

Antibody compositions are administered to subjects at concentrations from about 0.1 to 100 mg/ml, preferably from about 1 to 10 mg/ml. An antibody composition may be administered topically, intranasally, or via injection, e.g., intravenous, intraperitoneal, intramuscular, intraocular, or subcutaneous. A preferred mode of administration is injection. The administration may occur in a single injection or an infusion over time, i.e., about 10 minutes to 24 hours, preferably 30 minutes to about 6 hours. An effective dosage may be administered one time or by a series of injections. Repeat dosages may be administered twice a day, once a day, once a week, bi-weekly, tri-weekly, once a month, or once every three months, depending on the pharmacokinetics, pharmacodynamics and clinical indications. Therapy may be continued for extended periods of time, even in the absence of any symptoms.

A purified antibody composition may comprise polyclonal or monoclonal antibodies. An antibody composition may contain antibodies of multiple isotypes or antibodies of a single isotype. An antibody composition may contain unmodified chimeric antibodies, or the antibodies may have been modified in some way, e.g., chemically or enzymatically. An antibody composition may contain unmodified human antibodies, or the human antibodies may have been modified in some way, e.g., chemically or enzymatically. Thus an antibody composition may contain intact Ig molecules or fragments thereof, i.e., Fab, F(ab')$_2$, or Fc domains.

Administration of an antibody composition against an infectious agent, alone or in combination with another therapeutic agent, results in the elimination of the infectious agent from the subject. The administration of an antibody composition reduces the number of infectious organisms present in the subject 10 to 100 fold and preferably 1,000 fold, and more than 1,000 fold.

Similarly, administration of an antibody composition against cancer cells, alone or in combination with another chemotherapeutic agent, results in the elimination of cancer cells from the subject. The administration of an antibody composition reduces the number of cancer cells present in the subject 10 to 100 fold and preferably 1,000 fold, and more than 1,000 fold.

In certain aspects of the invention, an antibody may also be utilized to bind and neutralize antigenic molecules, either soluble or cell surface bound. Such neutralization may enhance clearance of the antigenic molecule from circulation. Target antigenic molecules for neutralization include, but are not limited to, toxins, endocrine molecules, cytokines, chemokines, complement proteins, bacteria, viruses, fungi, and parasites. Such an antibody may be administered alone or in combination with other therapeutic agents including other antibodies, other biological drugs, or chemical agents.

It is also contemplated that an antibody of the present invention may be used to enhance or inhibit cell surface receptor signaling. An antibody specific for a cell surface receptor may be utilized as a therapeutic agent or a research tool. Examples of cell surface receptors include, but are not limited to, immune cell receptors, adenosine receptors, adrenergic receptors, angiotensin receptors, dopamine and serotonin receptors, chemokine receptors, cytokine receptors, histamine receptors, etc. Such an antibody may be administered alone or in combination with other therapeutic agents including other antibodies, other biological drugs, or chemical agents.

It is also contemplated that an antibody of the present invention may be further modified to enhance therapeutic potential. Modifications may include direct- and/or indirect-conjugation to chemicals such as chemotherapeutic agents, radioisotopes, siRNAs, double-stranded RNAs, etc. Other modifications may include Fc regions engineered for either increased or decreased antibody-dependent cellular cytotoxicity, either increased or decreased complement-dependent cytotoxicity, or increased or decreased circulating half-life.

In other embodiments, an antibody may be used as a diagnostic agent for the detection one of the above diseases or disorders. A chimeric antibody may be detected using a secondary detection agent that recognizes a portion of the antibody, such as an Fc or Fab domain. In the case of the constant region, the portion recognized may be a CH1, CH2, or a CH3 domain. The Cκ and Cλ domain may also be recognized for detection. Immunohistochemical assays, such as evaluating tissue distribution of the target antigen, may take advantage of the chimeric nature of an antibody of the present invention. For example, when evaluating a human tissue sample, the secondary detection agent reagent recognizes the non-human portion of the Ig molecule, thereby reducing background or non-specific binding to human Ig molecules that may be present in the tissue sample.

Pharmaceutical Compositions and Kits

The present invention further relates to pharmaceutical compositions and methods of use. The pharmaceutical compositions of the present invention include an antibody, or an antigen-binding fragment thereof, in a pharmaceutically acceptable carrier. Pharmaceutical compositions may be administered in vivo for the treatment or prevention of a disease or disorder. Furthermore, pharmaceutical compositions comprising an antibody, or an antigen-binding fragment thereof, of the present invention may include one or more agents for use in combination, or may be administered in conjunction with one or more agents.

The present invention also provides kits relating to any of the antibodies, or antigen-binding fragments thereof, and/or methods described herein. Kits of the present invention may be used for diagnostic or treatment methods. A kit of the present invention may further provide instructions for use of a composition or antibody and packaging.

A kit of the present invention may include devices, reagents, containers or other components. Furthermore, a kit of the present invention may also require the use of an apparatus, instrument or device, including a computer.

EXAMPLES

The following examples are provided as further illustrations and not limitations of the present invention. The teachings of all references, patents and published applications cited throughout this application, as well as the Figures are hereby incorporated by reference.

Example 1

Construction of BAC C5P12

A BAC vector is based on the F-factor found in *E. coli*. The F-factor and the BAC vector derived from it are maintained as low copy plasmids, generally found as one or two copies per cell depending upon its life cycle. Both F-factor and BAC vector show the fi+ phenotype, which excludes an additional copy of the plasmid in the cell. By this mechanism, when *E. coli* already carries and maintains one BAC, and then an additional BAC is introduced into the *E. coli*, the cell maintains only one BAC, either the BAC previously existing in the cell or the external BAC newly introduced. This feature is extremely useful for selectively isolating BACs homologously recombined as described below.

The homologous recombination in *E. coli* requires the functional RecA gene product. In this example, the RecA gene had a temperature-sensitive mutation (recA$^{ts}$) so that the RecA protein was only functional when the incubation temperature was below 37° C. When the incubation temperature was above 37° C., the Rec A protein was non-functional or had greatly reduced recombination activity. This temperature sensitive recombination allowed manipulation of RecA function in *E. coli* so as to activate conditional homologous recombination only when it was desired. It is also possible to obtain, select or engineer cold-sensitive mutations of Rec A protein such that the protein is only functional above a certain temperature, e.g., 37° C. In that condition, the *E. coli* would be grown at a lower temperature, albeit with a slower generation time, and recombination would be triggered by incubating at above 37° C. for a short period of time to allow only a short interval of recombination.

Homologous recombination in *E. coli* was carried out by providing overlapping DNA substrates that are found in two circular BACs. BAC P12 (California Institute of Technology BAC library) was 182 kb in total size of which 172 kb was an insert of human genomic DNA comprising human Vκ genes (from IGKV1-5 to IGKV1-12, FIG. 1). BAC P12 was carried by pBeloBAC2 vector that had a zeocin resistant gene Zeo$^R$. BAC C5 (California Institute of Technology BAC library) carried a kanamycin resistance transposon cassette (kan$^R$) for selection in *E. coli*, KAN-2 (Epicentre Biotechnologies). BAC C5 was 225 kb in total size of which 218 kb was an insert of human genomic DNA comprising human Vκ genes (from IGKV4-1 to IGK1-6), the Jκ cluster, Cκ and 3' regulatory elements. BACs C5 and P12 carried a 70 kb of homology in the insert DNA. BAC C5 was carried in *E. coli* recAts.

Purified BAC P12 DNA was electroporated into *E. coli* recA$^{ts}$ carrying BAC C5. The cells were incubated at 30° C., the permissive temperature for recA$^{ts}$ activity, for 30 minutes. *E. coli* carrying homologous recombinants of the two BACs (kan$^R$zeo$^R$) were selected by plating on plates of selective low salt LB medium (Invitrogen) containing zeocin (50 ug/ml) and kanamycin (25 ug/ml) and incubated at 40° C., a non-permissive temperature for the recAts activity. Homologous recombinants in the 70 kb homology shared between C5 and P12 produced a single BAC of 407 kb in total size, of which 320 kb represents the recombined inserts of C5 and P12 (FIG. 1). As expected, the homologous recombination event created a duplication of the 70 kb overlap, one copy of which was situated between the repeated copies of the pBeloBAC vector sequences and the other copy now joining the two fragments of human DNA from the Igκ locus into one contiguous segment (FIG. 1). *E. coli* colonies that grew on the double-selection plates exhibited kan$^R$zeo$^R$, were picked and BAC DNA isolated by miniprep. BAC DNA was digested with NotI and run on pulse-field gels. Clones exhibited the expected pattern of bands (FIG. 2, left BAC map and left gel photo).

Figure 2:
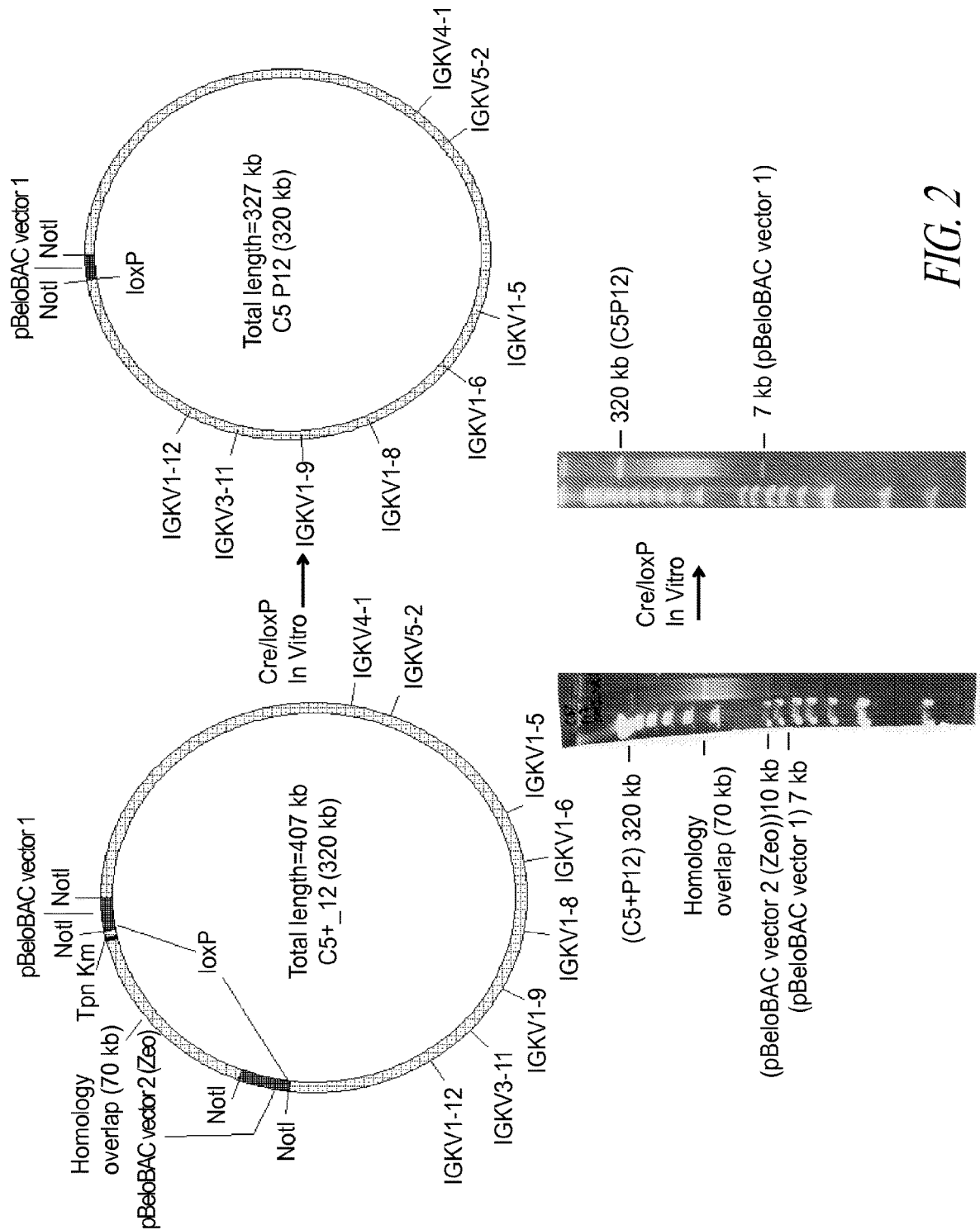
FIG. 2 depicts the removal of the 70 kb repeat between the two copies of the pBeloBAC vector using CRE-recombinase.

The 70 kb repeat between the two copies of the pBeloBAC vector was excised by using CRE-recombinase acting on the two loxP sites that exist on pBeloBAC (FIG. 2). Purified BAC (C5+P12) DNA was treated with CRE recombinase (New England Biolabs) in vitro according to the manufacturer's recommended conditions. The treated DNA was introduced into a RecA deficient (recA$^-$) strain of *E. coli* via electroporation and the resulting bacteria plated on chloramphenicol (Cm) containing plates and incubated at 37° C. All of the pBeloBAC vectors carry Cm$^R$ gene. The resolved BAC had lost the duplication of the 70 kb overlap and the sequence for pBeloBAC vector 2 (FIG. 2, right hand BAC map). The correctly resolved BAC lost both markers of Zeo$^R$ and Km$^R$.

Figure 3:
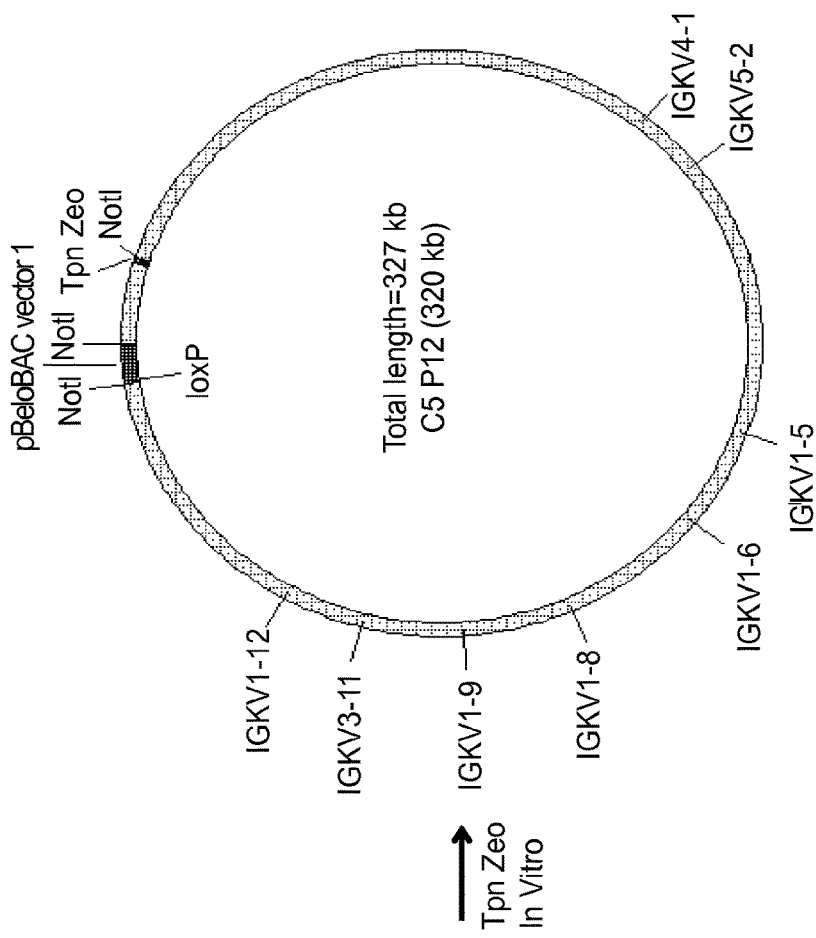
FIG. 3 depicts the insertion of Tpn-Zeo 15 kb from the junction of the vector.
Figure 3:
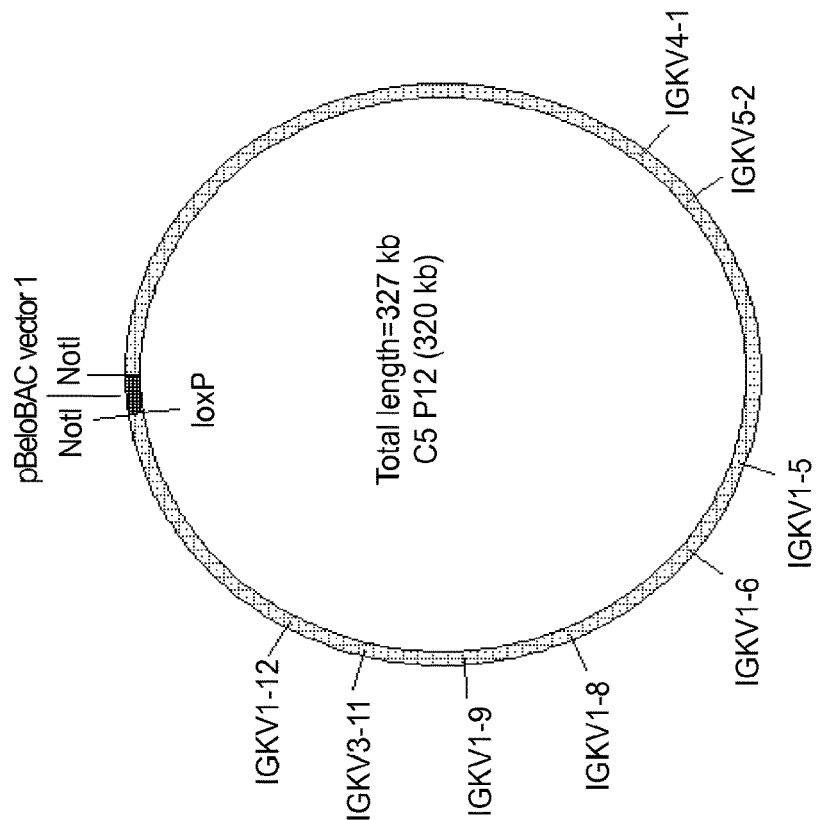

*E. coli* colonies that grew on plates exhibited Cm$^R$, were picked and BAC DNA was isolated by miniprep. BAC DNA was digested with NotI and run on pulse-field gels. Clones exhibited the expected pattern of bands (FIG. 2, right BAC map and right gel photo). The resolved BAC (C5P12) was 327 kb in total size of which 320 kb is human genomic DNA from, in 5' to 3' order, Vκ1-12 through the 3' cis regulatory regions, including 8 functional Vκ genes, the entire Jκ cluster and Cκ. To make the BAC (see, C5P12C20 in EXAMPLE 2), Tpn-Zeo was inserted at 15 kb from the junction of the vector (FIG. 3). Tpn-Zeo was constructed by inserting Zeo$^R$ gene into Transposon Construction Vector (Epicentre Biotechnologies), pMOD-3<R6Kγori/MCS> plasmid.

Example 2

Construction of a 489 Kb BAC Comprising the Majority of the Human Igκ Locus

Homologous recombination in *E. coli* was carried out by providing overlapping DNA substrates that are found in two circular BACs. BAC C20 (California Institute of Technology BAC library) was 218 kb in total size of which 206 kb was an insert of human genomic DNA comprising human Vκ genes. BAC C20 carried the KAN-2 kanamycin resistance transposon cassette (kan$^R$) for selection in *E. coli*. BAC C5P12 made in Example 1 carried a zeocin resistance transposon cassette (zeo$^R$) for selection in *E. coli*. C20 and C5P12 carried a 44 kb of native homology in the insert DNA. BAC C5P12 was carried in *E. coli* recA$^{ts}$.

Purified BAC C20 DNA was electroporated into *E. coli* recA$^{ts}$ carrying BAC C5P12. The cells were incubated at 30° C., the permissive temperature for recA$^{ts}$ activity, for 30 minutes. The fi+ phenotype conferred by the pBeloBAC vector prohibited the maintenance of more than one BAC in the cell, resulting in a population of *E. coli* carrying only C20 (kan$^R$zeo$^S$), only C5P12 (kan$^S$zeo$^R$), recombinants between the two BACs (kan$^R$zeo$^R$) or no BAC (kan$^S$zeo$^S$). *E. coli* carrying homologous recombinants of the two BACs were selected by plating on plates of selective low salt LB medium (Invitrogen) containing zeocin (50 ug/ml) and kanamycin (25 ug/ml) and incubated at 40° C., a non-permissive temperature for the recA$^{ts}$ activity.

Figure 4:
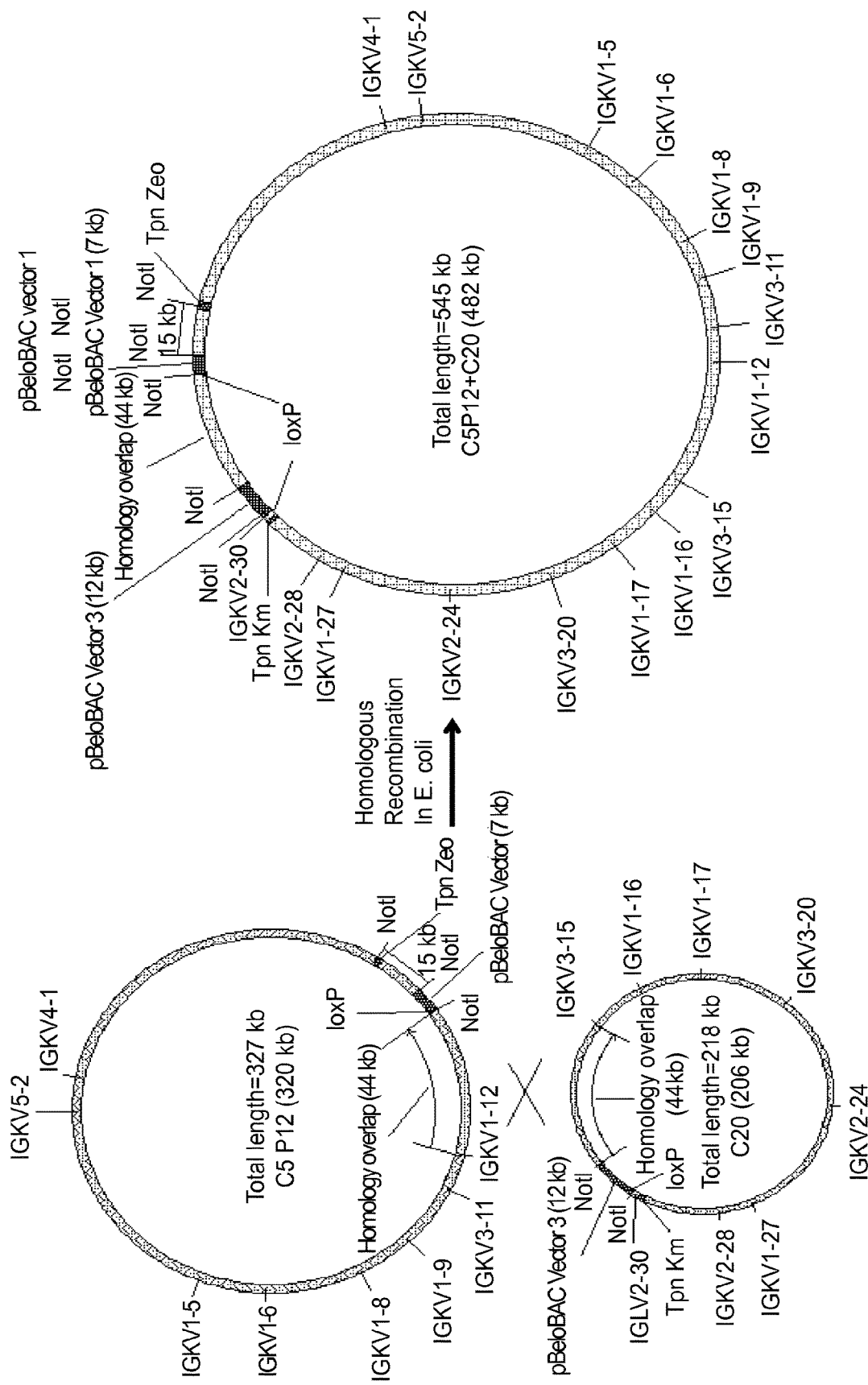
FIG. 4 depicts homologous recombination of BAC C5P12 and BAC C20 in *E. coli*.

Homologous recombinants in the 44 kb homology shared between C20 and C5P12 produced a single BAC of 545 kb in total size ("C"), of which 482 kb represents the recombined inserts of C20 and C5P12 (see FIG. 4). As expected, the homologous recombination event created a duplication of the 44 kb overlap, one copy of which was situated between the repeated copies of the pBeloBAC vector sequences and the other copy now joining the two fragments of human DNA from the Igκ locus into one contiguous segment (FIG. 4).

*E. coli* colonies that grew on the double-selection plates exhibited kan$^R$zeo$^R$, were picked and BAC DNA isolated by miniprep. BAC DNA was digested with NotI and run on pulse-field gels. Clones exhibited the expected pattern of bands (FIG. 5, left BAC map and left gel photo).

Figure 5:
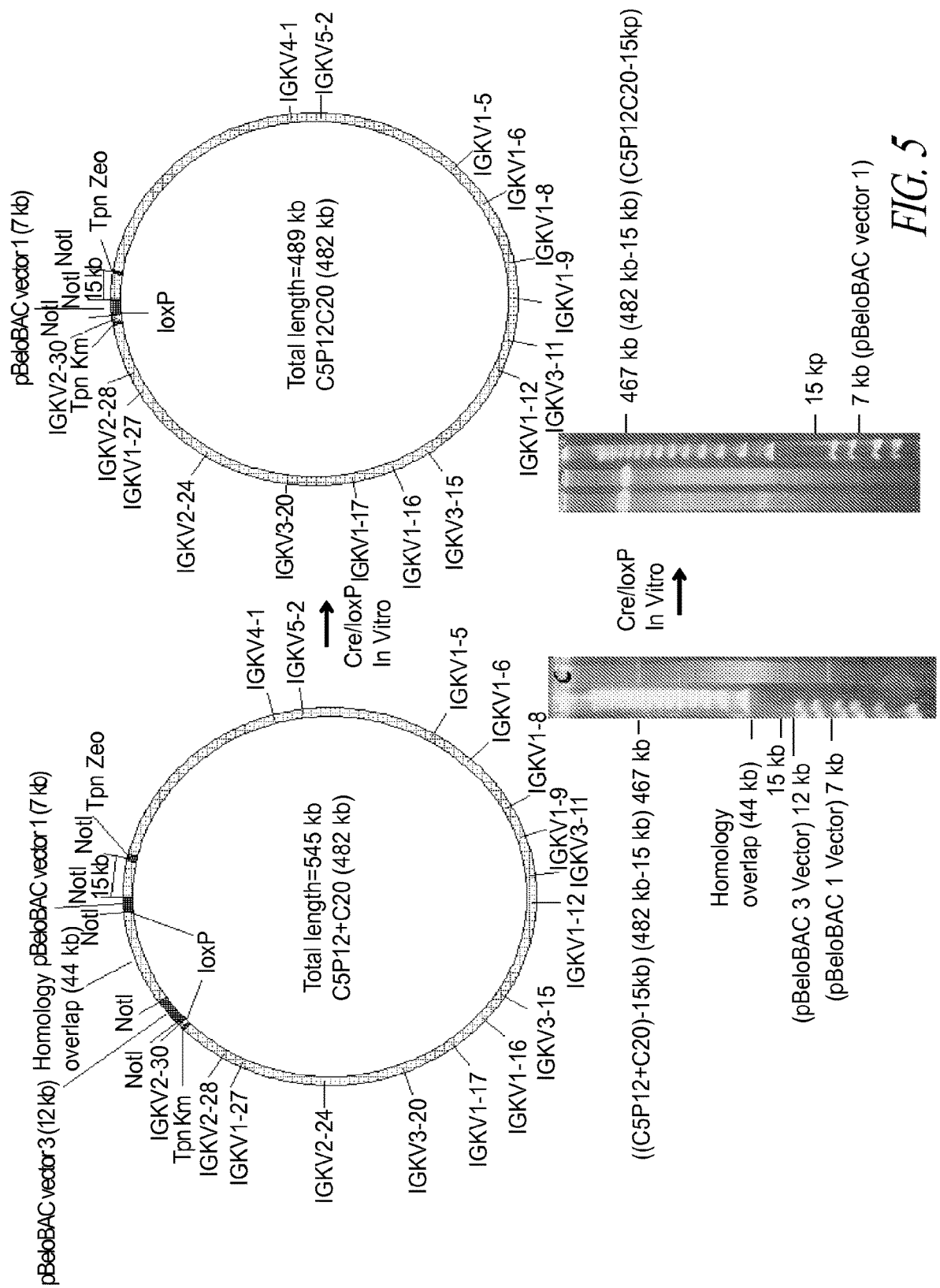
FIG. 5 depicts the removal of the 44 kb repeat between the two copies of the pBeloBAC vector using CRE-recombinase.

The 44 kb repeat between the two copies of the pBeloBAC vector was excised by using CRE-recombinase acting on the two loxP sites that exist on pBeloBAC (FIG. 5). Purified BAC C DNA was treated with CRE recombinase (New England Biolabs) in vitro according to the manufacturer's recommended conditions. The treated DNA was introduced into a RecA deficient (recA$^-$) strain of *E. coli* via electroporation and the resulting bacteria plated on zeocin/kanamycin double-selection plates as above and incubated at 37° C.

The resolved BAC had lost the duplication of the 44 kb overlap and the sequence for pBeloBAC vector 3 (FIG. 5, right hand BAC map). *E. coli* colonies that grew on the double-selection plates exhibited Km$^R$zeo$^R$, were picked and BAC DNA isolated by miniprep. BAC DNA was digested with NotI and run on pulse-field gels. Clones exhibited the expected pattern of bands (FIG. 5, right BAC map and right gel photo). The resolved BAC was 489 kb in total size of which 467 kb is human genomic DNA from, in 5' to 3' order, Vκ2-30 through the 3' cis regulatory regions, including 16 functional Vκ genes, the entire Jκ cluster and Cκ.

Example 3

In Silico Assembly of the Sequence of a Functional 194 Kb Synthetic Human Ig Lambda Light Chain Transgene The complete annotated sequence of the human immunoglobulin lambda light chain locus (Igλ) is available. For example see GenBank (http://www.ncbi.nlm.nih.gov/genbank/) Accession Number NG_000002. Additional detailed information, including bibliographic supporting scientific references is available at several public domain websites including Vbase (http://vbase.mrc-cpe.cam.ac.uk/) and IMGT (http://imgt.cines.fr/). This information includes data for the genetic and phenotypic content of the human Igλ locus, for instance including, but not limited to, identification of expressed gene sequences, pseudogenes, allelic variants, and which genes may encode domains prone to misfolding.

Using such public information, it is possible to assemble DNA sequences in silico using commonly available software for manipulating DNA sequences (e.g., MacVector, DNA-SIS) that encode a human Igλ light locus comprising only expressed human Vλ genes in operational linkage with from one to all 7 human Jλ-Cλ pairs and the complete functional human Igλ 3' enhancer (3' E). Cis regulatory elements controlling Vλ gene expression may be captured on as little as 500 bp of DNA immediately 5' to the start of the 5' untranslated region (UTR) and 500 bp or less DNA immediately 3' to the recombination signal sequence (RSS) immediately 3' of the end of the coding sequence of each Vλ gene. Preferably, a larger region of DNA 5' of the start of the 5' UTR may be used to increase the distance between V gene segments and to capture fully any and all cis regulatory elements.

Furthermore, the region between the most 3' of the human Vλ genes (V3-1) and Jλ1-Cλ1, the first Jλ-Cλ pair, and through the 3' E is captured in germline configuration. Alternatively, the distance of the sequence between Vλ3-1 and Jλ1-Cλ1 and/or the distance between Jλ7-Cλ7, the last Jλ-Cλ pair in the human locus, and the 3' E may be truncated. The specific distances are not so important as capturing of desired coding elements and critical cis regulatory elements including splice acceptors and splice donors, RSSs, intronic enhancer and 3' enhancer, preferably all 3 DNAseI hypersensitive sites. Furthermore, the human Igλ pseudogenes, Jλ4-Cλ4, Jλ5-Cλ5 and/or Jλ6-Cλ6 may be excluded from the in silico assembled sequence. There is a de minimus requirement for one functional Jλ-Cλ pair, either Jλ1-Cλ1, Jλ2-Cλ2, Jλ3-Cλ3 or Jλ7-Cλ7.

Specific restriction enzyme sites may be introduced at the end of the sequence. Specific restriction enzymes sites also may be introduced or deleted internally through sequence insertion, deletion or modification so long as they do not perturb gene expression or coding. These enzymes sites may include sequences useful for assembling the synthesized sequence in vitro, excising the DNA from the vector or for various screening methodologies, such as Southern blot of agarose gel using standard electrophoresis, field inversion gel electrophoresis (FIGE), and pulsed-field gel electrophoresis (PFGE).

Inserted sequences may also include primer binding sites to facilitate PCR-based screening methods including qPCR, for the desired and intact integration into the genome. Optionally, a site-specific recombinase site(s) such as loxP or any of its variants or frt are introduced to facilitate deletion of intervening sequences to make a single-copy transgene, to facilitate introduction of additional DNA via site specific recombination, or to facilitate other genetic engineering designs as known in the art. Also optionally included may be sequences for drug-selection cassettes for mammalian cells such as a positive selection marker for resistance to a drug such as hygromycin or a negative selection cassette such as thymidine kinase.

Using the strategy outlined above, a core 191 kilobase sequence ("Lambda Prime") was assembled in silico, comprising 29 functional human Vλ genes on approximately ~5 kb units, all 7 human Jλ-Cλ pairs and the human 3' Igλ locus enhancer, with the 57 kilobase sequence between Vλ3-1 and the human 3' Enhancer in germline configuration. The 29 chosen human Vλ genes were documented to be expressed in humans and present in all known human haplotypes as determined by investigation of the scientific literature. Sequences for the most commonly used alleles that encode variable regions that fold properly were chosen.

In instances in which two functional Vλ genes were positioned in proximity of less than 5 kb distance in the human germline configuration the entire sequence comprising the two Vλ genes, from approximately 4 kb 5' of the 5' UTR of the most 5' gene and approximately 500 bp 3' of the RSS of the most 3' Vλ gene, was used. The coding and non-coding regions of the sequence were sufficient to drive proper developmental regulation and expression and to generate a diversity of human Igλ light chains once introduced into the mouse genome.

A sequence for a hygromycin resistance expression cassette was inserted 5' of the most 5' Vλ cassette. For ease of excision from the BAC vector and for confirming intact integration, rare cutting restriction enzymes were inserted into the sequence, at the 5' end, recognition sequences for StuI/EcoRV/AsiSI/PvuI and AgeI/PacI/AseI/BsaBI sites 5' and 3' of the $hyg^R$ cassette, respectively, and at the 3' end downstream of the 3' enhancer, recognition sequences for AsiSI, AleI, EcoRI, Bsa BI were inserted.

Example 4

In Silico Assembly of the Sequence of Two Synthetic Human Ig Lambda Light Chain Transgenes Derived from the Sequence of Ig Lambda-Prime Using the Lambda-Prime sequence described in Example 3, two additional transgenes were designed. A core 94 kilobase sequence ("Lambda 3") was assembled in silico, comprising 8 functional human Vλ genes on approximately ~5 kb units, all 7 human Jλ-Cλ pairs and the human 3' Igλ locus enhancer, with the 57 kilobase sequence between Vλ3-1 and the human 3' Enhancer in germline configuration. The 8 chosen human Vλ genes were documented to be expressed in humans. Sequences for the most commonly used alleles that encode variable regions that fold properly were chosen. The coding and non-coding regions of the sequence were sufficient to drive proper developmental regulation and expression and to generate a diversity of human Igλ light chains once introduced into the mouse genome. An frt site was inserted 5' of the most 5' Vλ gene cassette. For ease of excision from the BAC vector and for confirming intact integration, rare cutting restriction enzymes were inserted into the sequence, at the 5' end, recognition sequences for ApaLI/AvrII/EcoRI sites were inserted 5' of the frt site and a recognitions sequence for FseI was inserted 3' of the frt site and, at the 3' end, the recognition sequences for AsiSI, AleI, EcoRI, Bsa BI described in Example 3 were retained.

Using the Lambda-Prime sequence described in Example 3, a sequence ("Lambda 5") was assembled in silico comprising 21 human Vλ genes with demonstrated expression and functionality, and with no known non-functional alleles or haplotypic variation across individual humans. The Vλ cassettes were generally approximately 5 kb in size. The coding and non-coding regions of the sequence were sufficient to drive proper development regulation and expression and to generate a diversity of human Igλ light chains once introduced into the mouse genome in operational linkage with any DNA construct comprising at least one functional Jλ-Cλ pair and preferably a functional 3' E. Sequences for the most commonly used alleles that encode variable regions that fold properly were chosen.

A sequence for a hygromycin resistance expression cassette 5' of the most 5' Vλ cassette as described in Example 3 was retained. The sequence for an frt site was inserted 3' of the most 3' Vλ cassette. For ease of excision from the BAC vector and for confirming intact integration, rare cutting restriction enzymes were inserted into the sequence, StuI/EcoRV/AsiSI/PvuI sites 5' of the $hyg^R$ cassette, AgeI/PacI/AseI/BsaBI sites 3' of the $hyg^R$ cassette, as described in Example 3, and FseI/PvuI sites 5' of the frt site and KpnI/NheI sites 3' of the frt site.

Example 5

Synthesis and Assembly of DNAs Comprising the Lambda 3 and Lambda 5 Transgenes

DNAs of greater than approximately 30-40 kb in size are carried on BACs. Example 2 documents the creation of a BAC 545 kb in size. In addition, other cloning vectors capable of carrying large pieces of DNA such as YACs, PACs, MACs, may be used. Genetic engineering and physical recovery of large DNAs in all of these vectors is well-documented in the literature.

Contract service providers synthesize and assemble very large pieces of DNA. The DNA sequence of Lambda 3 was transmitted to DNA2.0, Inc. (Menlo Park, Calif.). The sequence was synthesized into physical DNA and assembled. The final fully assembled sequence was carried in a BAC with pBeloBAC as the vector backbone. The full BAC was sequenced by SeqWright, Inc. (Houston, Tex.) using 454 sequencing technology (454 Life Sciences, Roche). The sequence of the synthetic Lambda 3 DNA was confirmed against the reference sequence. Six sequence deviations from the in silico sequence were likely 454 sequencing read errors due to long homopolymeric or dipolymeric sequences. The deviations, even though very likely not mutations in the actual physical synthetic DNA, mapped to non-coding, non-regulatory regions.

The DNA sequence of Lambda 5 was transmitted to DNA2.0, Inc. (Menlo Park, Calif.). The sequence was synthesized and assembled. The final fully assembled sequence was carried in a BAC with pBeloBAC as the vector backbone. The full BAC was sequenced by SeqWright, Inc. (Houston, Tex.) using 454 sequencing technology (454 Life Sciences, Roche). The sequence of the synthetic Lambda 5 DNA was confirmed against the reference sequence. Minimal deviations from the in silico sequence were found. Any deviations were likely 454 sequencing read errors due to long homopolymeric or dipolymeric sequences. The deviations, even though very likely not mutations in the actual physical synthetic DNA, map to non-coding, non-regulatory regions.

Example 6

Generation of Transgenic Mice Carrying the Synthetic Lambda 3 Transgene

The Lambda 3 BAC was digested with FseI and AsiSI and the synthetic human Lambda 3 insert purified from the vector sequence by pulse-field gel electrophoresis. The 94 kb gel band containing the Lambda 3 sequence was excised from the gel and purified from the gel. The purified, concentrated DNA was microinjected into the pronucleus of fertilized mouse eggs. Of 758 embryos transferred, 138 live mice were born. PCR assays to detect human Igλ sequence comprising the 5' and 3' ends and in the middle of the Lambda 3 transgene were used to screen DNAs isolated from tail tissue from mouse pups to screen for the presence of DNA at the 5', 3' and the middle of the Lambda 3 transgene. Twenty-four mouse pups were confirmed positive for all three PCR products. ELISA specific for human Igλ was performed on serum samples from the founder mice. Twenty independent founder mice were found to have significant circulating levels of human Igλ in their serum, confirming function of the Lambda 3 transgene. Founder mice were bred to produce transgenic offspring.

Example 7

Expression of a Diversity of Human Ig Lambda Light Chains from the Synthetic Human Lambda 3 Transgene in Mice Samples of serum from the transgenic offspring of the founder mice are confirmed to have the intact and expressed Lambda 3 transgene as described in Example 6.

Blood is drawn from Lambda 3 transgenic mice and collected in heparinized tubes. Lymphocytes are separated and concentrated via density gradient centrifugation over Lympholyte M. The lymphocytes are treated with fluorochrome-conjugated antibodies against a mouse B cell marker, e.g., B220 or CD19, and an antibody specific for human Igλ. Mouse B cells expressing human Igλ light chains on their surface are detected by FACs. The percentage of human Igλ positive B cells ranges from 1 to 40% or more.

mRNA is isolated from lymphoid tissue, e.g., spleen, lymph nodes, bone marrow, blood, of the Lambda 3 transgenic mice and RT-PCR using primers specific for human Vλ and Cλ is used to amplify the expressed repertoire of human variable regions from the Lambda 3 transgene. The Vλ cDNAs are cloned into a cloning vector such as TA (Invitrogen, Inc., Carlsbad, Calif.). The human Vλ cDNAs are sequenced. All 8 Vλ genes and the functional human Jλ-Cλ are shown to be represented in the expressed repertoire. The sequence of the cDNAs have an open-reading frame and encode fully human variable regions, consistent with functional recombination of the Vλ-Jλ and appropriate development regulation of the human Igλ transgene.

Mice transgenic for Lambda 3 are immunized with antigen using methods known in the art. mRNA is isolated from the secondary lymphoid tissue, e.g., spleen, lymph nodes, of the Lambda 3 transgenic mice and RT-PCR using primers specific for human Vλ and Cλ is used to amplify the expressed repertoire of human variable regions from the Lambda 3 transgene. The Vλ cDNAs are cloned into a cloning vector such as TA. The human Vλ cDNAs are sequenced. The human Vλ regions are found to be mutated as compared to the germline sequence, indicative of somatic mutation events consistent with affinity maturation.

Taken together these data demonstrate that the Lambda 3 transgene is expressed in B cells, expresses a diversity of human Igλ light chains, and is a template for somatic mutation events indicative of it undergoing affinity maturation in the secondary immune response.

Example 8

Generation of Transgenic Mice Carrying a 194 Kb Synthetic Human Ig Lambda Transgene, Lambda-Prime, by Pronuclear Co-Microinjection The synthetic, sequence confirmed Lambda 5 BAC is digested with AsiSI and FseI, run on an agarose gel in PFGE and DNA comprising the Lambda 5 sequence is isolated as in Example 6. This DNA is co-microinjected with DNA comprising the Lambda 3 sequence, isolated as in Example 6, into the pro-nucleus of fertilized mouse eggs. The co-microinjected DNA co-integrates into the mouse genome, with a significant proportion of the integration events comprising Lambda 5 and Lambda 3 oriented in operable linkage, i.e., both are oriented in the same 5' to 3' orientation respective to each other and Lambda 5 is integrated 5' to Lambda 3, i.e., the 3' end of Lambda 5 is juxtaposed to the 5' end of Lambda 3. Thus, the contiguous human sequence of Lambda-Prime, 194 kb of synthetic DNA in operable linkage is created, comprising 29 functional human Vλ sequences, all human Jλ-Cλ and the human 3' enhancer sequence. Intact integration in operably linkage is confirmed by Southern blots of genomic DNAs cut with rare cutting restriction enzymes, run on standard and PGFE gels and probed with sequences specific to Lambda 5 and Lambda 3. Because the full nucleotide sequence of an operably-linked co-integrated Lambda-Prime sequence is fully known, in silico prediction of restriction fragment patterns is readily accomplished to confirm intact and operable linkage, as facilitated by the rare-cutting restriction enzyme sites designed into the sequences as outlined in Example 4. Transgene function is confirmed by ELISA for human Igλ in the serum.

Founder mice are bred and transgenic offspring are produced. Copy number is readily assessed by methods such as qPCR or densitometric scanning of Southern blots of genomic DNA. If desired, in lines in which multi-copy Lambda 5-3 transgenes are integrated, transgenic mice are bred to transgenic mice expressing FLP-recombinase. The frt sites present in the Lambda 5 and Lambda 3 transgenes recombine site-specifically, particular in the germline cells. Gametes are produced that have a resolved single-copy transgene of Lambda 5-Lambda 3 operably linked and these gametes transmit the single-copy resolved Lambda-Prime sequence into the next generation.

Transgenic mice, either multicopy or single copy, are tested for Lambda Prime function as described in Example 7. The data demonstrate that the Lambda-Prime transgene is expressed in B cells, expresses a diversity of human Igλ light chains, and is a template for somatic mutation events indicative of it undergoing affinity maturation in the secondary immune response.

Example 9

Generation of Transgenic Mice Carrying a 194 Kb Synthetic Human Ig Lambda Transgene by Co-Transfection Into ES Cells DNAs comprising the Lambda 3 and the Lambda 5 sequences are isolated as in Example 8. These DNAs are co-introduced into mouse ES cells by a method such as lipofection or electroporation. The presence of a positive-selectable maker cassette 5' of the most 5' Vλ gene on Lambda 5, e.g., hygromycin, enables positive selection for integration of Lambda 5. The co-introduced DNA randomly co-integrates into the mouse genome, with a significant proportion of the integration events comprising Lambda 5 and Lambda 3 oriented in operable linkage, i.e., both are oriented in the same 5' to 3' orientation respective to each other and Lambda 5 is integrated 5' to Lambda 3', i.e., the 3' end of Lambda 5 is juxtaposed to the 5' end of Lambda 3. Thus, the contiguous Lambda-Prime sequence of 194 kb of synthetic DNA in operable linkage is created.

Intact integration in operably linkage is confirmed by Southern blots of genomic DNAs cut with rare cutting restriction enzymes, run on standard and PGFE gels and probed with sequences specific to Lambda 5 and Lambda 3. Because the full nucleotide sequence of an operably-linked co-integrated Lambda-Prime sequence is fully known, in silico prediction of restriction fragment patterns is readily accomplished to confirm intact and operable linkage, as facilitated by the rare-cutting restriction enzyme sites designed into the sequences as outlined in Example 4. Copy number may be readily assessed by methods such as qPCR or densitometric scanning of Southern blots of genomic DNA. If desired, in clones in which multi-copy Lambda 5-3 transgenes are integrated, FLP-recombinase is transiently expressed in the clones. The frt sites present in the Lambda 5 and Lambda 3 transgenes recombine site-specifically. Clones are produced that have a resolved single-copy transgene of Lambda 5-Lambda 3 operably linked.

ES cells carrying the operably linked Lambda-Prime transgene sequence are used to generate transgenic mice using well-established methods. For examples, ES cells are microinjected into mouse blastocysts, which are then implanted in pseudo-pregnant foster females. Chimeric pups are born. Chimeric mice are bred and the resulting offspring are screened for the presence of the Lambda-Prime transgene.

Transgenic mice, either multicopy or single copy, are tested for Lambda-Prime function as described in Example 7. The data demonstrate that the Lambda-Prime transgene is expressed in B cells, expresses a diversity of human Igλ light chains, and is a template for somatic mutation events indicative of it undergoing affinity maturation in the secondary immune response.

Example 10

Synthesis and Assembly of a DNA Comprising the Lambda-Prime Transgene and Generation of Transgenic Mice Therefrom DNAs of greater than approximately 30-40 kb in size are carried on BACs. Example 2 documents the creation of a BAC 545 kb in size. In addition, other cloning vectors capable of carrying large pieces of DNA such as YACs, PACs, MACs, may be used. Genetic engineering and physical recovery of large DNAs in all of these vectors is well-documented in the literature.

Contract service providers synthesize and assemble very large pieces of DNA. The DNA sequence of Lambda-Prime is transmitted to one search service provider, DNA2.0, Inc. (Menlo Park, Calif.). The sequence is synthesized into physical DNA and assembled. The final fully assembled sequence is carried in a BAC with pBeloBAC as the vector backbone. The full BAC was sequenced by sequencing service providers such as SeqWright, Inc. (Houston, Tex.) using 454 sequencing technology (454 Life Sciences, Roche) or standard shotgun sequencing. The sequence of the synthetic Lambda-Prime DNA is confirmed against the reference sequence. Any sequence deviations from the in silico sequence are likely sequencing read errors due to long homopolymeric or dipolymeric sequences. The deviations, even though very likely not mutations in the actual physical synthetic DNA, map to non-coding, non-regulatory regions.

Alternatively, Lambda 3 and Lambda 5 may be recombined in vitro using techniques as described in Examples 1 and 2. They may also be recombined using other methods of engineering BACs such as recombineering, or standard restriction fragment ligation into pBeloBAC following by transfection into E. coli.

Transgenic mice are generated as described in Examples 6 or by introduction into ES cells such as by electroporation, lipofection etc., as exemplified in Example 9. Transgenic mice, either multicopy or single copy, are tested for Lambda-Prime function as described in Example 8. The data demonstrate that the Lambda-Prime transgene is expressed in B cells, expresses a diversity of human Igλ light chains, and is a template for somatic mutation events indicative of it undergoing affinity maturation in the secondary immune response.

Example 11

Creation of a Human IgL Transgene Via Co-Introduction of Lambda 3 with Genomic DNA Comprising Additional Human V Lambda Repertoire Libraries of human genomic DNA are available commercially or through licensing and are well-characterized. These include the CalTech human genomic library carried on BACs and various human genomic DNA libraries on YACs. The CalTech human library BAC clones from libraries B, C and D may be ordered through Invitrogen (Carlsbad, Calif.). Human genomic libraries are also available carried on cosmids, phage, P1s, PACs etc. All of these vectors may be modified prior to co-introduction using techniques readily available in the art.

Because of the ready facility by which large fragments of DNA may be sequenced, the genomic inserts on these BACs or YACs may be sequenced confirmed using a contract service provider as described above. The complete human DNA insert may be isolated. Alternatively, a subfragment may be isolated using rare-cutting restriction enzyme sites available in the genomic DNA. An example of a suitable YAC is L1 (U.S. Pat. No. 7,435,871). Other YAC, BAC and cosmid clones suitable for use are described in Kawasaki et al., (*Gen. Res.* (1995) 5: 125-135) and Frippiat et al. (*Hum. Mol. Genet.* (1995) 4: 983-991). One or more BACs or YACs comprising additional human Vλ genes are co-introduced with the Lambda 3 construct. Optionally, the Lambda 3 DNA is co-introduced with two or more other constructs with additional Vλ genes. The two or more co-introduced constructs are confirmed to co-integrate in operable linkage as outlined in Examples 8 and 9. Transgene functionality is confirmed as in Example 7. Thus, a human Igλ transgene may be partly synthetic and partly derived from a genomic library, with the core Jλ-Cλ and 3' cis regulatory sequences created by synthetic means and all or part of the Vλ repertoire derived from a genomic library.

Example 12

Creation of a Human IgL Transgene Via Co-Introduction of Lambda 5 with a Genomic DNA Sequence Comprising at Least One Functional Human JL-CL Pair Libraries of human genomic DNA are available commercially or through licensing and are well-characterized. These include the CalTech human genomic library carried on BACs and various human genomic DNA libraries on YACs. The CalTech human library BAC clones from libraries B, C and D may be ordered through Invitrogen (Carlsbad, Calif.). Human genomic libraries are also available carried on cosmids, phage, P1s, PACs etc. All of these vectors may be modified prior to co-introduction using techniques readily available in the art.

Because of the ready facility by which large fragments of DNA may be sequenced, the genomic inserts on these BACs or YACs may be sequenced confirmed using a contract service provider as described above. The complete human DNA insert may be isolated. Alternatively, a subfragment may be isolated using rare-cutting restriction enzyme sites available in the genomic DNA. An example of a suitable YAC is L2 (U.S. Pat. No. 7,435,871), which contains all 7 Jλ-Cλ pairs and the human 3' enhancer. Other YAC, BAC and cosmid clones suitable for use are described in Kawasaki et al., (*Gen. Res.* (1995) 5: 125-135) and Frippiat et al. (*Hum. Mol. Genet.* (1995) 4: 983-991).

The core construct contains at least one functional human Jλ-Cλ pair and preferably a functional 3' enhancer. The Lambda 5 DNA is co-introduced with the isolated DNA of the core construct and, optionally, one or more other constructs with additional Vλ genes. The two or more co-introduced constructs are confirmed to co-integrate in operable linkage as outlined in Examples 8 and 8. Transgene functionality is confirmed as in Example 7. Thus, a human Igλ transgene may be partly synthetic and partly derived from a genomic library, with the core Jλ-Cλ and 3' cis regulatory sequences derived from a genomic library and all or part of the Vλ repertoire created by synthetic means.

Example 13

Use of Cre-Lox System to Recombine Transgenes

The sequence of the Lambda 3 transgene is designed in silico as described in Example 4 with the alteration of an addition of a loxP site or variant thereof replacing the sequence of the frt site or being place adjacent to it, and a drug-resistance cassette activity in mammalian cells such as puromycin-resistance is inserted 5' to the loxP site, creating Lambda 3P. The Lambda 3P sequence is synthesized and assembled into physical DNA as described in Example 5. The Lambda 3P DNA is isolated from the vector DNA, introduced into ES cells, puromycin-resistance colonies selected for, picked and molecularly screened for intact integration of Lambda 3P.

The sequence of the Lambda 5 transgene is designed in silico as described in Example 4 with the alteration of an addition of a loxP site or variant thereof replacing the sequence of the frt site or being place adjacent to it, creating Lambda 3P. The Lambda 5P sequence is synthesized and assembled into physical DNA as described in Example 5 except that the BAC vector sequence, such as pBeloBAC, has a deleted loxP site or carries a version incompatible for recombination with that in the Lambda 5P sequence. The circular Lambda 5P BAC DNA is isolated and co-transfected with CRE recombinase into Lambda 3P ES clones. The CRE recombinase engenders site-specific recombination between the loxP sites, resulting in integration of the Lambda 5P DNA in operably linkage upstream of the Lambda 3 DNA, therein reconstituting the Lambda Prime sequence. Lambda 5P positive ES clones are selected for puromycin-resistance, picked and molecularly screened for insertion of Lambda 5P into Lambda 3P as described in Example 9. Transgenic mice are generated from the ES cells and confirmed for Lambda Prime transgene function as described in Example 9.

This process for insertion of additional Vλ repertoire upstream of a functional core Jλ-Cλ sequence is applicable for any vector existing as a circular DNA, e.g., plasmid, cosmid, BAC, or circularizable, such as a YAC, so long as the loxP site is 3' of most 3' Vλ gene desired to be operably linked to the Jλ-Cλ core sequence.

Example 15

Generation of Mice Transgenic Expressing Human Ig Lambda from a Synthetic DNA Transgene Comprising a Highly Chimeric Human-Mouse DNA Sequence The annotated sequence of the mouse immunoglobulin lambda light chain locus is available in the public domain, see Genbank accession number NC_000082. Because of the unique structure of the mouse Igλ locus, which is composed of two separates units (see Seising et al., *Immunoglobulin Genes* 1989 Acad. Press Ltd., pp. 111-122), the sequence of one of the mouse Igλ locus units is selected. A 60,000 nucleotide (nt) sequence comprising 4 kb upstream of the start codon of Vλ1 and 5 kb downstream of the 3' enhancer is isolated in silico. A sub-sequence of 4 kb upstream of the start codon of mouse Vλ2 and 500 bp downstream of the RSS is identified ("VX expression cassette"). FIG. 1 of Ramsden and Wu (*Proc. Natl. Acad. Sci.* 1991 88: 10721-10725) identifies the Vλ2 RSS and the RSS for Jλ3 and Jλ1. The sequence of the 39 nucleotide RSS of Vλ1 of mouse is replaced in the functional orientation with the functional RSS from a human Vλ, e.g., Vλ3-1. This approximately 5,000 nucleotide sequence comprising 4,000 nt upstream of the start codon, human RSS and through 500 nt downstream of the RSS, is the core Vλ expression construct.

The 28 nucleotide sequence of mouse Jλ3 and Jλ1 are replaced in the functional orientation with the functional RSS from human Jλ3 and Jλ1. The coding sequences for mouse Jλ3 and Jλ1 are replaced by the coding sequences for human Jλ3 and Jλ1. The coding sequences for mouse Cλ3 and Cλ1 are replaced by the coding sequences for human Cλ3 and Cλ1. The coding sequence of mouse Vλ1 is replaced with the coding sequence of a human Vλ gene, e.g., Vλ3-1. The sequence comprising the mouse 3' enhancer is replaced with 7,562 nucleotide sequence comprising the 3 DNAseI hypersensitive sites of the human Igλ 3' enhancer. This sequence is the core chimeric IgI construct. Combriato and Klobeck (*J. Immunol.* 2002 168:1259-1266) teach other sequence changes for restoring optimal enhancer activity to the mouse 3' enhancer.

Additional Vλ repertoire is added in silico through appending the core Vλ expression construct sequence 5' to the core chimeric Igλ construct. In each appended Vλ expression construct, the mouse Vλ1 coding sequence is replaced with human Vλ coding sequence. The entire human Vλ repertoire can be appended sequentially in silico yielding a sequence of approximately 205,000 nt.

The sequence or two portions thereof is synthesized and assembled into physical DNA is described in previous examples. The DNA is used to construct transgenic mice as described in previous examples. Transgenic mice are analyzed for transgene expression and function as described in previous examples. The data demonstrate that the transgene is expressed in B cells, expresses a diversity of human Igλ light chains, and is a template for somatic mutation events indicative of it undergoing affinity maturation in the secondary immune response.

The preceding example illustrates the methodology by which exquisitely precisely and complexly engineered sequences are composed in silico and then a process for making transgenic animals comprising that sequence. The methodology is not limited to the described sequence.

Example 14

In Silico Assembly of the Sequence of a Functional Synthetic Human Ig Kappa Light Chain Transgene The methodologies described in the preceding examples are broadly applicable for the in silico assembly and subsequent synthesis of any sequence up to the cloning capacity of a BAC, which as demonstrated in Example 2, is at least 500 kb. As described in Example 3, a sequence encoding a human Igκ transgene was assembled from publicly available information on the sequence of the human and mouse Igκ loci. The annotated sequence for the complete human Igκ locus was accessed from Genbank, accession number NG_000834. The sequence comprises the complete proximal Vκ cluster through the 3' regulatory elements, 3' enhancer, Ed and RS. Additional detailed information, including bibliographic supporting scientific references is available at several public domain websites including Vbase (http://vbase.mrc-cpe.cam.ac.uk/) and IMGT (http://imgt.cines.fr/). This information includes data for the genetic and phenotypic content of the human Igκ locus, for instance including, but not limited to, identification of expressed gene sequences, pseudogenes, allelic variants, and which genes may encode domains prone to misfolding.

A 30,000 nt sequence comprising 4 kb upstream of human Vκ4-1 through the complete human Jκ cluster through 1,000 nt 3' of human Cκ was in germline configuration. Appended in silico 3' of human Cκ was a 25,600 nt germline configured mouse DNA sequence comprising the Igκ 3' enhancer, Ed and RS. This sequence served as the core Igκ expression cassette.

To expand the repertoire, sequence for additional Vκ expression cassettes as units of ~5,000 nt were added 5' of Vκ4-1. In instances in which two functional Vκ genes were positioned in proximity of less than 5 kb distance in the human germline configuration the entire sequence comprising the two Vκ genes, from approximately 4 kb 5' of the 5' UTR of the most 5' gene and approximately 500 bp 3' of the RSS of the most 3' Vκ gene, was used. As described in Example 3, recognition sequences for specific restriction enzymes were introduced at the ends of the sequence. Recognition sequences for specific restriction enzymes were introduced and deleted internally through sequence insertion, deletion or modification; these did not perturb gene expression or coding.

Example 16

Generation of Mice Transgenic for a Locus Expressing Human Igk, Said Locus Comprising Synthetic DNA Using methodology described in any of the preceding Examples 1-2 and Examples 4-14 and the process for in silico assembly of sequences described in Examples 3 and 15, physical DNA that encodes human Igκ light chains is synthesized and used to create transgenic mice. Transgenic mice are analyzed for transgene expression and function as described in previous examples using appropriate reagents for use in studying human Igκ expression at the nucleic acid and protein levels. The data demonstrate that the transgene is expressed in B cells, expresses a diversity of human Igκ light chains, and is a template for somatic mutation events indicative of it undergoing affinity maturation in the secondary immune response.

Example 17

Generation of Mice Expressing Human Igk from a Synthetic DNA Transgene Comprising a Highly Chimeric Human-Mouse DNA Sequence The annotated sequence of the human immunoglobulin kappa light chain locus is publicly available, see Genbank accession number NG_000834. The annotated sequence of the mouse immunoglobulin kappa light chain locus is publicly available, see Genbank accession number NC_005612. Other sources such as the IGMT Repertoire website (http://imgt.cines.fr/) are used as a resource on the map and functionality of individual components in the loci. A mouse DNA sequence of approximately 50,000 bases, comprising a Vκ, preferably the most proximal mouse Vκ, Vκ3-1, the Jκ cluster, Cκ through 3' regulatory regions, is isolated in silico. Though this sequence is preferably in germline configuration, intergenic regions of DNA may be deleted to make a smaller overall sequence so long as critical regulatory regions such as the Igκ intronic enhancer, 3' enhancer, Ed and RS, the sequence and location of which are all documented publicly, are unpertubed.

The mouse exons for the Vκ, Jκ and Cκ are replaced with their human counterparts. The human Vκ exons replacing the mouse Vκ exons may be Vκ4-1, which is human Vκ most proximal to the human Jκ cluster but this is not absolutely necessary. Any human Vκ exon sequences may be used. It is noted that human Vκ4-1 and the next most proximal Vκ gene, Vκ5-2, are inverted 3'-5' relative to the human Jκ cluster in the germline configuration. The human Vκ 4-1 exons would be oriented in the mouse Vκ context in the 5'-3' orientation relative to the mouse Jκ locus in the sequence constructed in silico. The mouse Jκ locus comprises 5 Jκ sequences but Jκ3 may not be expressed because of a non-canonical donor splice sequence. The human Jκ locus comprises 5 Jκ sequences, all of which are functional. Incorporation of the human Jκ3 exon would bring with it the proper splice donor sequence, particular for splicing to its counterpart splice acceptor sequence on human Cκ.

Additional Vκ repertoire is added in silico through identifying approximately 5 kb units comprising in proximal to distal order the functional mouse Vκ genes. This number of 5 kb sequence units is equivalent to the number of human Vκ genes to be represented in the transgenes. Mouse pseudogenes are eliminated. In each appended Vκ expression construct, the mouse Vκ coding sequence is replaced with human Vκ coding sequence. The 5 kb unit may also be a repeated unit so that identical non-coding sequences comprise each unit and the units are only distinguished by the unique human Vκ exon sequence. Each unit is appended onto the core sequence 5' to the preceding one, sequentially building the sequence of the artificial locus, proximally to distally.

The entire proximal human Vκ repertoire can be appended sequentially in silico yielding a sequence of approximately 140,000 bases. The inverted distal cluster of human Vκ genes may also be included, though because they are duplications of the genes in the proximal cluster, they contribute to <10% of the expressed human Igκ repertoire, and because they are missing in some human haplotypes, their inclusion is not necessary and may be undesired for later antibody drug development.

The sequence or two portions thereof is synthesized and assembled into physical DNA is described in previous examples. The DNA is used to construct transgenic mice as described in previous examples. Transgenic mice are analyzed for transgene expression and function as described in previous examples. The data demonstrate that the transgene is expressed in B cells, expresses a diversity of human Igκ light chains, and is a template for somatic mutation events indicative of it undergoing affinity maturation in the secondary immune response.

The preceding example illustrates the methodology by which exquisitely precisely and complexly engineered sequences are composed in silico and then a process for making transgenic animals comprising that sequence. The methodology is not limited to the described sequence.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A mouse whose genome comprises a transgene encoding a polypeptide comprising a human immunoglobulin heavy chain variable region, wherein the transgene comprises (1) a plurality of immunoglobulin heavy chain variable (V) exons encoding human immunoglobulin heavy chain V polypeptides, (2) mouse immunoglobulin non-coding sequences between the V exons, (3) a plurality of immunoglobulin heavy chain diversity (D) coding sequences encoding human immunoglobulin heavy chain D polypeptides, (4) mouse immunoglobulin non-coding sequences between the D coding sequences, (5) a plurality of immunoglobulin heavy chain joining (J) coding sequences encoding human immunoglobulin heavy chain polypeptides, and (6) mouse immunoglobulin non-coding sequences between the J coding sequences, wherein the transgene is capable of undergoing gene arrangement and thereby upon expression to produce a polypeptide comprising the human immunoglobulin heavy chain variable region.

2. The mouse according to claim 1, wherein the mouse immunoglobulin non-coding sequences between the V exons are mouse immunoglobulin heavy chain non-coding sequences.

3. The mouse according to claim 1, wherein the mouse immunoglobulin non-coding sequences between the D coding sequences are mouse immunoglobulin heavy chain non-coding sequences.

4. The mouse according to claim 1, wherein the mouse immunoglobulin non-coding sequences between the J coding sequences are mouse immunoglobulin heavy chain non-coding sequences.

5. The mouse according to claim 1, wherein the non-coding sequences between the V exons, the non-coding sequences between the D coding sequences and the non-coding sequences between the J coding sequences are selected from the group consisting of an intron and cis regulatory sequences.

6. The mouse according to claim 5, wherein the cis regulatory sequences are selected from promoters, enhancers, recombination signal sequences, splice acceptor sequences and splice donor sequences.

7. The mouse according to claim 1, wherein the transgene is a synthetic transgene.

8. The mouse according to claim 1, wherein the mouse immunoglobulin non-coding sequences between the V exons are mouse immunoglobulin light chain non-coding sequences.

9. The mouse according to claim 1, wherein the mouse immunoglobulin non-coding sequences between the D coding sequences are mouse immunoglobulin light chain non-coding sequences.

10. The mouse according to claim 1, wherein the mouse immunoglobulin non-coding sequences between the J coding sequences are mouse immunoglobulin light chain non-coding sequences.

11. The mouse according to claim 1, wherein the transgene further comprises one or more coding sequences encoding a human or mouse immunoglobulin heavy chain constant (C) polypeptide.

12. The mouse according to claim 11, wherein the one or more coding sequences encoding the immunoglobulin heavy chain C polypeptide encode a mouse heavy chain C polypeptide.

13. The mouse according to claim 1, wherein the transgene further comprises mouse non-coding sequences upstream of the V exons.

14. The mouse according to claim 1, wherein the transgene further comprises mouse non-coding sequences downstream of the J coding sequences.

15. The mouse according to claim 13, wherein the non-coding sequences upstream of the V exons are selected from promoters and enhancers.

16. The mouse according to claim 14, wherein the non-coding sequences downstream of the J coding sequences are selected from polyadenylation sites and 3' untranslated regions.

17. The mouse according to claim 1, wherein the genome further comprises a second transgene encoding a human light chain, or a portion thereof.

18. The mouse according to claim 17, wherein the human light chain is a kappa light chain or a lambda light chain.

19. The mouse according to claim 1, wherein the transgene comprises (1) a plurality of immunoglobulin heavy chain variable (V) exons encoding human immunoglobulin heavy chain V polypeptides, (2) mouse immunoglobulin heavy chain non-coding sequences between the V exons, (3) a plurality of immunoglobulin heavy chain diversity (D) coding sequences encoding human immunoglobulin heavy chain D polypeptides, (4) mouse immunoglobulin heavy chain non-coding sequences between the D coding sequences, (5) a plurality of immunoglobulin heavy chain joining (J) coding sequences encoding human immunoglobulin heavy chain J polypeptides, and (6) mouse immunoglobulin heavy chain non-coding sequences between the J coding sequences; and (7) one or more coding sequences encoding immunoglobulin mouse heavy chain constant (C) polypeptides.

* * * * *

UNITED STATES PATENT AND TRADEMARK OFFICE
CERTIFICATE OF CORRECTION

PATENT NO. : 10,604,587 B2
APPLICATION NO. : 15/463800
DATED : March 31, 2020
INVENTOR(S) : Green et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Twenty-fourth Day of November, 2020

Andrei Iancu
*Director of the United States Patent and Trademark Office*